(12) United States Patent
Bui et al.

(10) Patent No.: US 10,422,724 B2
(45) Date of Patent: Sep. 24, 2019

(54) MICROTOME WASTE REMOVAL ASSEMBLY

(71) Applicant: Sakura Finetek U.S.A., Inc., Torrance, CA (US)

(72) Inventors: Xuan S. Bui, Torrance, CA (US); Alyicia Marie Rios, Downey, CA (US); Erico Von Bueren, Rolling Hills Estates, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 0 days.

(21) Appl. No.: 15/811,447

(22) Filed: Nov. 13, 2017

(65) Prior Publication Data

US 2018/0136087 A1 May 17, 2018

Related U.S. Application Data

(60) Provisional application No. 62/421,755, filed on Nov. 14, 2016.

(51) Int. Cl.
*G01N 1/06* (2006.01)
*B26D 7/01* (2006.01)
*B26D 7/27* (2006.01)
*H05B 33/08* (2006.01)
(Continued)

(52) U.S. Cl.
CPC .............. *G01N 1/06* (2013.01); *B26D 7/015* (2013.01); *B26D 7/27* (2013.01); *H05B 33/0845* (2013.01); *G01N 21/255* (2013.01); *G01N 2001/061* (2013.01); *G01N 2001/065* (2013.01); *G01N 2001/066* (2013.01); *G01N 2001/068* (2013.01);
(Continued)

(58) Field of Classification Search
CPC ............. G01N 1/06; B26D 7/27; B26D 7/015
See application file for complete search history.

(56) References Cited

U.S. PATENT DOCUMENTS 2,473,753 A 6/1949 Johnson
3,103,844 A 9/1963 Persson
(Continued)

FOREIGN PATENT DOCUMENTS

| CN | 201583423 | 9/2010 |
|---|---|---|
| EP | 0145011 | 6/1985 |
| WO | WO-2012147730 | 11/2012 |

OTHER PUBLICATIONS

"Reichert Jung", Ultracut Manual, Retrieved from the Internet: http://ablab.ucsf.edu/sites/ablab.ucsf.edu/files/Reichert-jung%20Ultracult%20ultramicrotome%20instruction%20manual%20u.pdf, Oct. 21, 2014.
(Continued)

*Primary Examiner* — Sean M Michalski
(74) *Attorney, Agent, or Firm* — William Thomas Babbitt; Leech Tishman Fuscaldo & Lampl

(57) ABSTRACT

A sample sectioning device including a housing having a base member, a cutting mechanism positioned on the base member and operable to cut sections from a sample, a sample holder dimensioned to hold a sample and operable to move with respect to the cutting mechanism during a cutting operation, and a waste removal assembly positioned below the cutting mechanism and the sample holder, the waste removal assembly having a first member and a second member that are dimensioned to remove waste produced during the cutting operation.

16 Claims, 26 Drawing Sheets

(51) Int. Cl.
*G01N 1/31* (2006.01)
*G01N 21/25* (2006.01)
(52) U.S. Cl.
CPC .............. *G01N 2001/315* (2013.01); *G01N 2201/0627* (2013.01)

(56) References Cited

U.S. PATENT DOCUMENTS

| | | | |
|---|---|---|---|
| 3,212,379 A * | 10/1965 | McCormick | G01N 1/06 83/167 |
| 3,680,420 A * | 8/1972 | Blum | G01N 1/06 83/167 |
| 4,051,755 A * | 10/1977 | Raveed | G01N 1/06 83/167 |
| 4,269,092 A * | 5/1981 | Disharoon | G01N 1/06 83/42 |
| 4,317,401 A * | 3/1982 | Disharoon | B23P 15/40 225/2 |
| 4,485,706 A * | 12/1984 | Disharoon | B23P 15/40 30/350 |
| 4,511,224 A | 4/1985 | Sitte et al. | |
| 5,226,335 A * | 7/1993 | Sitte | G01N 1/06 83/703 |
| 5,461,953 A * | 10/1995 | McCormick | G01N 1/06 83/36 |
| 5,713,255 A * | 2/1998 | Izvozichikov | G01N 1/06 83/106 |
| 6,000,309 A * | 12/1999 | Gnagi | G01N 1/06 83/167 |
| 6,209,437 B1 | 4/2001 | Izvoztchikov et al. | |
| 6,253,653 B1 * | 7/2001 | Walter | G01N 1/06 83/703 |
| 6,330,348 B1 | 12/2001 | Kerschmann et al. | |
| 6,598,507 B1 | 7/2003 | Gunther et al. | |
| 7,146,895 B2 * | 12/2006 | Kong | G01N 1/06 83/705 |
| 7,273,000 B2 | 9/2007 | Thiem et al. | |
| 7,437,984 B2 * | 10/2008 | Gilchrist | G01N 1/06 83/703 |
| 8,001,876 B1 * | 8/2011 | Tabb | B26D 7/01 33/514.2 |
| 8,025,842 B2 | 9/2011 | Nakajima et al. | |
| 8,113,099 B2 * | 2/2012 | Lihl | G01N 1/06 83/490 |
| 8,166,855 B2 * | 5/2012 | Ito | G01N 1/06 83/109 |
| 8,245,613 B2 * | 8/2012 | Miyatani | G01N 1/06 83/112 |
| 8,312,796 B2 | 11/2012 | Kunkel et al. | |
| 8,640,585 B2 | 2/2014 | Zust et al. | |
| 8,687,858 B2 | 4/2014 | Walter et al. | |
| 2004/0035275 A1 | 2/2004 | Lihl et al. | |
| 2005/0072285 A1 * | 4/2005 | Lang | G01N 1/06 83/520 |
| 2009/0133556 A1 | 5/2009 | Ito et al. | |
| 2009/0165627 A1 * | 7/2009 | Walter | G01N 1/06 83/713 |
| 2013/0186248 A1 * | 7/2013 | Heid | G01N 1/06 83/530 |
| 2014/0026728 A1 | 1/2014 | Walter | |
| 2015/0008096 A1 * | 1/2015 | Ito | G02B 21/34 198/339.1 |
| 2015/0122093 A1 * | 5/2015 | Johe | G01N 1/06 83/13 |
| 2015/0143970 A1 * | 5/2015 | Johe | G01N 1/06 83/821 |
| 2017/0115189 A1 * | 4/2017 | Heid | G01N 1/06 |
| 2017/0284904 A1 * | 10/2017 | Lim | G01N 1/06 |

OTHER PUBLICATIONS

Jawitz, Martin W. et al., "Materials for Rigid and Flexible Printed Wiring Boards", Electrical and Computer Engineering, Sep. 22, 2006, 39-64.

Leica Microsystems, Leica EM UC7, Operating Manual, Version 16216032 Sep. 2010, Retrieved from the Internet: http://www.nuance.northwestern.edu/docs/epic-pdf/EM%20UC7%20instruction%20manual.pdf.

Sakura Finetek U.S.A., Inc., International Search Report and Written Opinion dated May 15, 2018, PCT Application No. PCT/US2017/061551.

Sakura Finetek U.S.A., Inc., Invitation to Pay Additional Fees and, Where Applicable, Protest Fee, dated Mar. 23, 2018, PCT Application No. PCT/US2017/061551.

Sakura Finetek U.S.A., Inc., Notice of Allowance dated Mar. 1, 2018, U.S. Appl. No. 15/811,476.

"Shimano Dynamo Front Hub 36h DH-3D72 Centerlock", Amazon.com, http://www.amazon.com/Shimano-Nexus-Dynamo-Bicycle-Hub/dp/B00OMB7236/ref=pd_sbs_468_5?ie=UTF8&dpID=41xmbm5BaPL&dpSrc=sims&preST=_AC_UL160_SR160%2C160_&refRID=1301RKTWXCC8EQFPPZQ6, Apr. 6, 2016, 1-5.

Jennova, "Energy Harvesting", http://jennova.com/index.php/products/energy-harvester, Apr. 6, 2016, 1-6.

\* cited by examiner

MICROTOME WASTE REMOVAL ASSEMBLY

CROSS-REFERENCE TO RELATED APPLICATION

The application is a non-provisional application of U.S. Provisional Application No. 62/421,755, filed Nov. 14, 2016 and incorporated herein by reference.

BACKGROUND

Field

Embodiments of the invention relate to microtomes or other tissue sample sectioning devices to produce sections of samples, specifically, some embodiments relate to microtomes or other tissue sample sectioning devices that have a light source, a generator, built in accessory storage, accessory tray, paraffin removal assembly and/or alarm.

Background Information

Histology is a science or discipline associated with the preparation of tissue specimens for examination or analysis. The examination or analysis may be of the cellular level, chemical composition, tissue morphology or composition, or other tissue characteristics.

In histology, a sample of tissue may be prepared for sectioning by a microtome or other sample sectioning device. Commonly, the tissue may be dried or dehydrated by removing most or almost all of the water from the tissue, for example by exposing the tissue to one or more dehydrating agents. After dehydrating the tissue, clearing of the dehydrating agents may be performed, and then an embedding agent (e.g., wax with added plasticizers) may be introduced or infiltrated into the dehydrated tissue. The removal of the water and the infiltration of the embedding agent may preserve the tissue specimen for ten (10) and more years and may aid in sectioning the tissue into thin sections using a microtome.

Embedding may then be performed on the tissue. During embedding, the tissue that has been dehydrated and infiltrated with the embedding agent may be embedded into a block using one of various waxes, or various polymers, or another embedding medium. Representatively, the dehydrated and wax-infiltrated tissue may be placed in a mold and/or cassette, melted wax may be dispensed over the tissue until the mold has been filled with the wax, and then the wax may be cooled and hardened. Embedding the tissue into a block of wax may help to provide additional support during cutting or sectioning of the tissue specimen with a microtome.

The microtome may be used to cut thin slices or sections of the sample of tissue. Various different types of microtomes are known in the arts. Representative types include, for example, sled, rotary, vibrating, saw, and laser microtomes. The microtomes may be manual or automated. Automated microtomes may include motorized systems or drive systems to drive or automate a cutting movement between the sample from which the sections are to be cut and a cutting mechanism used to cut the sections. Manual microtomes may rely upon rotation of a hand wheel to drive the cutting movement. It is to be appreciated that microtomes may also be used for other purposes besides just histology, and that microtomes may be used on other types of samples besides just embedded tissue.

SUMMARY

In some embodiments, the invention is directed to a sample sectioning device including a housing having a base member, a cutting mechanism positioned on the base member and operable to cut sections from a sample, a sample holder dimensioned to hold a sample and operable to move with respect to the cutting mechanism during a cutting operation, and a waste removal assembly positioned below the cutting mechanism and the sample holder, the waste removal assembly having a first member and a second member that are dimensioned to remove waste produced during the cutting operation. In some cases, the first member and the second member are each movably connected to the base member and operable to move between a first position in which they are at a first angle with respect to the base member and a second position in which they are at a second angle with respect to the base member, wherein the second angle is greater than the first angle. In some cases, the first member and the second member are operable to move with respect to the base member between a first angle of incline and a second angle of incline, wherein the second angle of incline is approximately 90 degrees and is greater than the first angle of incline. The cutting mechanism may be operable to slide with respect to the base member, and sliding of the cutting mechanism may cause the first member and the second member to move with respect to one another. The first member and the second member may form a pitched surface below the cutting mechanism and the sample holder. The first member and the second member may be fixed with respect to one another. The device may further include a temperature controlling member coupled to the first member or the second member to control a temperature thereof.

In other embodiments, the invention is directed to a waste removal assembly for a sample sectioning device including a first inclined member coupled to a microtome housing, a second inclined member coupled to a microtome housing, and an actuator movably coupled to the first inclined member and the second inclined member, and the actuator is operable to cause a slope of one of the first inclined member or the second inclined member to change. The first inclined member and the second inclined member may be metal plates. One of the first inclined member or the second inclined member may include a plate having an edge that is coupled to the sample sectioning device by a hinge. The slope of the first inclined member or the second inclined member may be a first slope, and the actuator may cause the first inclined member or the second inclined member to change to a second slope, and the second slope may be greater than the first slope. The actuator may cause the slope of one of the first inclined member or the second inclined member to change within a range of ninety degrees with respect to horizontal. The actuator may be a cutting mechanism of the sample sectioning device, and a sliding of the cutting mechanism causes the slope of one of the first inclined member or the second inclined member to change. In some cases, the actuator may include an actuating member and a protrusion, and the actuating member slides the protrusion under the first inclined member and the second inclined member to change the slope. The actuator may be manually operated by a user. The actuator may be automated. In some cases, a thermoelectric cooler (TEC) may be coupled to the first member or the second member to control a temperature thereof.

The above summary does not include an exhaustive list of all aspects of the present invention. It is contemplated that the invention includes all apparatuses that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE SEVERAL VIEWS OF THE DRAWINGS

The invention may best be understood by referring to the following description and accompanying drawings that are used to illustrate embodiments of the invention. In the drawings:

FIG. 11 illustrates a block diagram of one embodiment of a sample sectioning device that a sample holder is associated with.

DETAILED DESCRIPTION

In the following description, numerous specific details, such as particular microtomes, particular cutting drive systems, particular sensors, particular sensing mechanisms, particular surface orientation measurement and/or adjustment processes, and the like, are set forth. However, it is understood that embodiments of the invention may be practiced without these specific details. In other instances, well-known mechanical components, circuits, structures and techniques have not been shown in detail in order not to obscure the understanding of this description.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Figure 1:
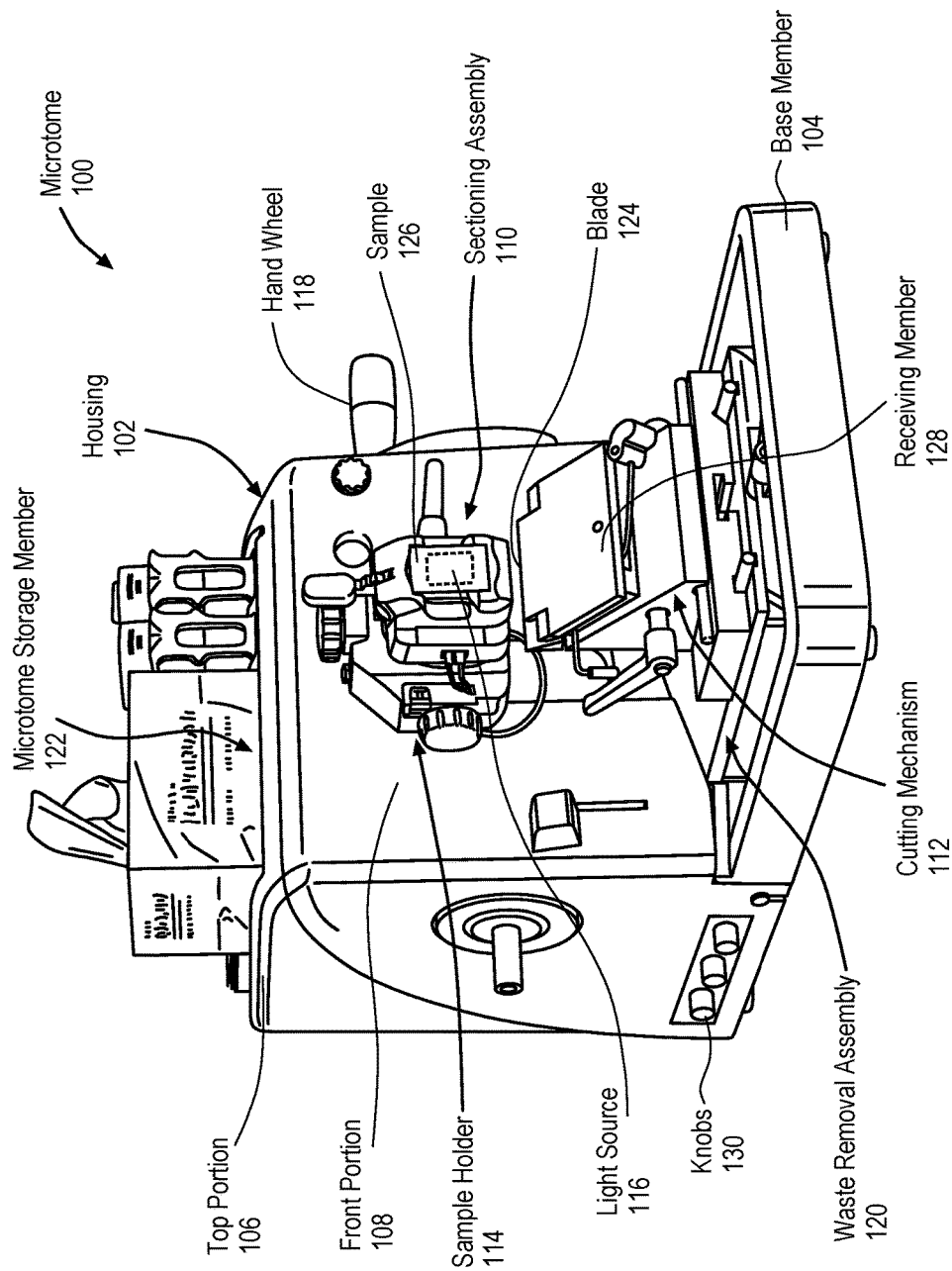
FIG. 1 illustrates a schematic view of an embodiment of a microtome or other sample sectioning device.

FIG. 1 illustrates a schematic view of an embodiment of a microtome or other sample sectioning device. Microtome 100 may be a manual microtome, while in another embodiment, microtome 100 may be an automated microtome. Microtome 100 may include an enclosure or housing 102 dimensioned to support and/or enclose various microtome components. For example, housing 102 may be a shell like structure, which defines an interior enclosed space or chamber, within which microtome components can be positioned and enclosed, and an outer surface for supporting microtome components. The housing 102 may include a base member 104, a top portion 106 and a front portion 108. The base member 104 is dimensioned to rest on a surface, such as a table, upon which the device is to be operated, and can support various sample sectioning instruments or components. The top portion 106 may be the upper most surface of the microtome housing 102, and in some cases, provide an area for storage of microtome accessories, as will be discussed herein. The front portion 108 connects the top portion 106 to the base member 104, and may support various sample sectioning components. For example, the sectioning assembly 110, which includes various components, instruments, or the like for sample sectioning, may be mounted to front portion 108 of housing 102. Representatively, sectioning assembly 110 may include a cutting mechanism 112 mounted to base member 104 and a sample holder 114 mounted to front portion 108 of housing 102. Sample holder 114 may be dimensioned to receive and hold a sample (e.g., a paraffin embedded tissue sample) during a cutting operation.

In addition, to facilitate viewing of the sample during a cutting operation, sample holder 114 may further include a light source 116. Light source 116 is configured to illuminate the sample 126 held within sample holder 114 from a back side (e.g., side facing and/or contacting sample holder 114) so that the user can more clearly see various aspects of sample 126 during a cutting operation. For example, the sample 126 could be a biological tissue that is taken from the body and embedded in paraffin wax. The tissue may include DNA, proteins, lipids, carbohydrates, fibers, connective tissue, or other types of tissue compounds or structures that can be highlighted, or otherwise made more visible, by the light source 116 shining there through. In addition, the light source 116 may help to highlight a location of the tissue within the paraffin wax so that the user can, for example, see whether the tissue is being sliced and/or how many more slices of the paraffin are necessary to reach the tissue. The light source 116 may be controlled using input devices 130 connected to microtome 100. Input devices 130 may, for example, be knobs, buttons, touch pads, or any other user input device that may be used to control an operation of an electronic component. The sample holder 114 and light source 116 configuration will be describe in more detail in reference to FIG. 2-FIG. 5.

Cutting mechanism 112 may include a cutting member such as a knife or blade 124 suitable for cutting slices of a sample 126 held within the sample holder 114. In one embodiment, sample holder 114 moves relative to cutting mechanism 112. For example, sample holder 114 may be coupled to a feed drive system or cutting drive system that is operable to move sample holder in a vertical direction (e.g., up and down with respect to horizontal) while cutting mechanism 112 remains stationary. Alternatively, sample holder 114 (or portions of sample holder 114) may remain stationary while cutting mechanism 112 is moved, for example in a vertical direction (e.g., up and down) with respect to sample holder 114. Regardless of which component is moved, the movement of sample holder 114 with respect to cutting mechanism 112 should be such that it causes the sample held within sample holder 114 to be sliced or sectioned. More specifically, a surface of sample 126 may be sufficiently aligned parallel with cutting mechanism 112 and/or a cutting plane associated with cutting mechanism 112 and then sample holder 114 (or cutting mechanism 112) moved up and/or down to produce sufficiently evenly cut sample sections. It should be noted that terms such as "horizontal", "vertical", "top", "bottom", "upper", "lower", and the like, are used herein to facilitate the description of the illustrated device. It is possible for other devices to replace horizontal movements with vertical movements, etc.

The sliced sample sections from sample 126 may be received by, for example, a sloped receiving member 128 coupled to blade 124. Sectioning assembly 110 may further be designed so that debris or waste (e.g., pieces of paraffin) associated with the slicing operation may fall behind cutting mechanism 112 and/or receiving member 128, and onto a waste removal assembly 120 positioned on base member 104, below sample holder 114. Waste removal assembly 120 will be described in more detail in reference to FIG. 17A-FIG. 20.

Microtome 100 may further include a storage member 122. Storage member 122 may include compartments or recessed regions that are designed to hold various microtome components. For example, storage member 122 may be configured to hold a tissue box, a slide, a carrier holding multiple slides or other instruments such as brushes or pencils a user may need while operating microtome 100. Storage member 122 may be integrally formed with the top portion 106 of microtome housing 102, may be a separate tray like structure that is removable attached to top portion 106, or a combination of an integrally formed member and a removable structure. Storage member 122 will be described in more detail in reference to FIG. 12-FIG. 16B.

Referring again to FIG. 1, the movement of sample holder 114 may be controlled using hand wheel 118 (or a control device in the case of an automated microtome). It should be understood that while only the handle portion of hand wheel 118 can be seen from this view, the handle portion is associated with a wheel that may be rotated upon rotation of the handle. Rotation of hand wheel 118 may cause a vertical drive member associated with sample holder 114 (or cutting mechanism 112) to move in a vertical direction to facilitate slicing of sample 126. In some embodiments, hand wheel 118 may be associated with a generator that is operable to convert a mechanical energy of hand wheel 118 into electrical energy to drive, for example, an operation of light source 116. Various aspects of hand wheel 118 and a generator will be discussed in more detail in reference to FIG. 6-FIG. 10.

Figure 2:
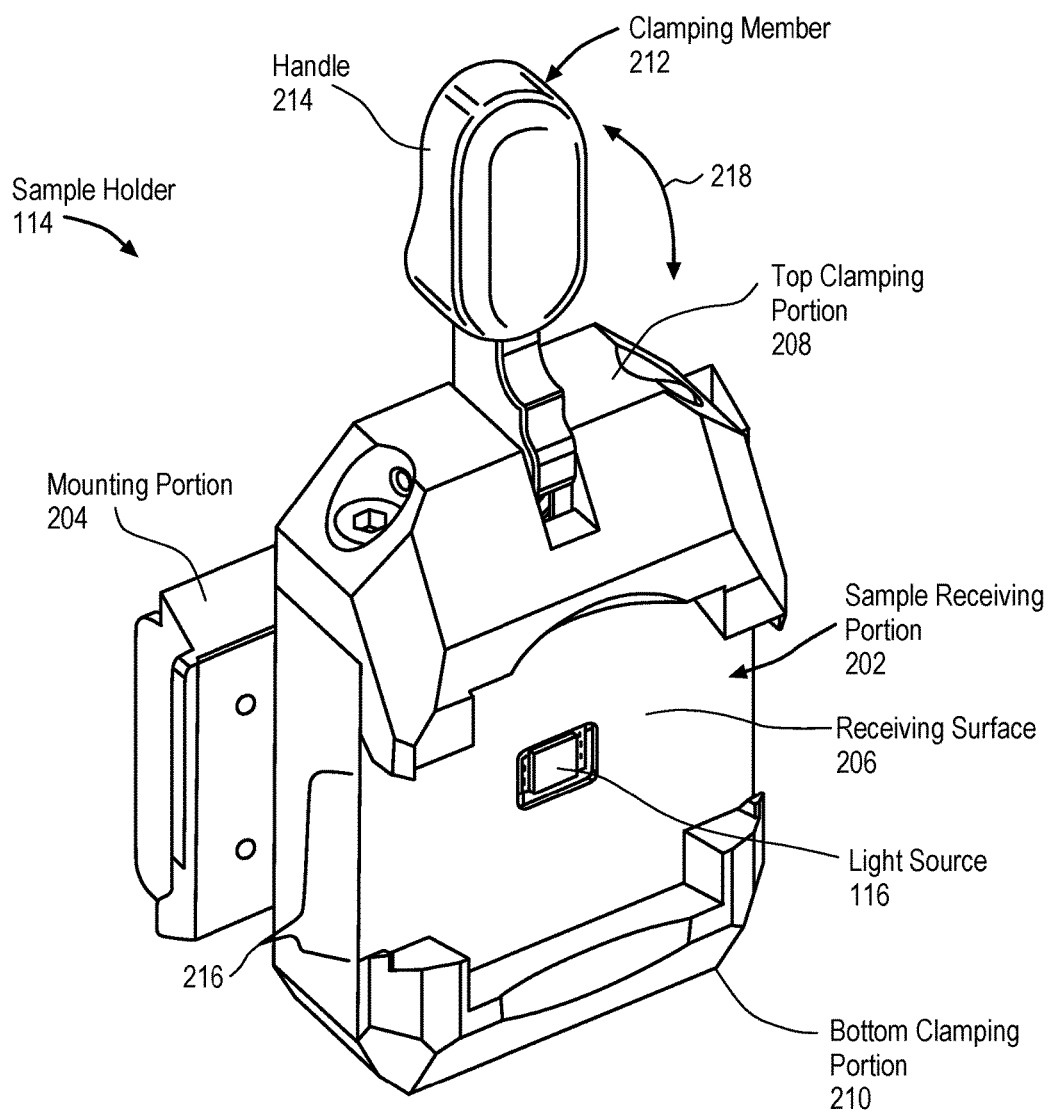
FIG. 2 illustrates one embodiment of a perspective view of a sample holder.

The specific aspects of sample holder and the associated light source will now be described in more detail in reference to FIG. 2, FIGS. 3A-3B, FIG. 4 and FIG. 5. In particular, FIG. 2 illustrates a perspective view of sample holder 114. Sample holder 114 may be considered part of, or may itself be, a microtome chuck. Sample holder 114 may include a sample receiving portion 202 dimensioned to receive and hold a sample, and a mounting portion 204 dimensioned to removably mount, or mate, sample holder 114 to the desired microtome. Sample receiving portion 204 may include a sample receiving surface 206 upon which the sample is to be positioned. The sample receiving surface 206 may be flanked by a top clamping portion 208 and a bottom clamping portion 210 which define a recessed region 216 within which the sample can be positioned. The top clamping portion 208 and the bottom clamping portion 210 may be considered part of clamping member 212. Clamping member 212 also includes a handle 214 that can be used to slide clamping portions 208, 210 toward or away from one another to change a size of the recessed region 216 within sample receiving portion 202, and in turn, clamp onto a sample positioned within recessed region 216. For example, during operation, the top and bottom clamping portions 208, 210 are caused to slide toward one another (e.g., along rails) by pivoting handle 214 along arrow 218 in a direction away from portion 202 to a first, extended position (as shown). In this position, portions 208, 210 create a recessed region 216 that is approximately same size as, or slightly smaller than, the sample, such that portions 208, 210 (which are biased toward one another) press against the sample edges, and hold the sample within recessed region 216. To release the sample from recessed region 216 of sample receiving portion 202, handle 214 is moved to a second, retracted position (e.g., pushed or pivoted forward along arrow 218), so that the top and bottom clamping portions 208, 210 slide away from one another, thereby increasing the size of the recessed region 216 and allowing for the sample to be removed. In other words, the pivoting movement of handle 214 forward or backward, in turn, drives a sliding movement of clamping portions 208, 210 away or toward one another, respectively. This movement in turn, further locks the sample within, or releases the sample from, recessed region 216 of sample receiving portion 202. It should be noted that while the illustrated position of handle 214 (e.g., the extended position) is described here as a position which causes portions 208, 210 to move away from one another, it is also contemplated that this position of handle 214 may, in other cases, move portions 208, 210 toward one another, to clamp a sample therebetween.

Light source 116 is positioned along sample receiving portion 202. Representatively, in one embodiment, light source 116 includes a light emitting chip, for example, one or more of a light-emitting sensor or light-emitting diode (LED) die or chip including one or more of a light-emitting diode (LED). The LED chip may be positioned along a surface of sample receiving portion 202, or within a cavity or recess formed within sample receiving portion 202. The light source 116 is therefore behind the sample when the sample is positioned within sample receiving portion 202. The light output by the LED passes through the sample and illuminates the sample from the back side, allowing for the various features of a biological tissue therein to be more easily examined. The specific aspects of light source 116 and the illumination of the sample from the back side is shown in FIG. 3A-FIG. 3B.

Figure 3A:
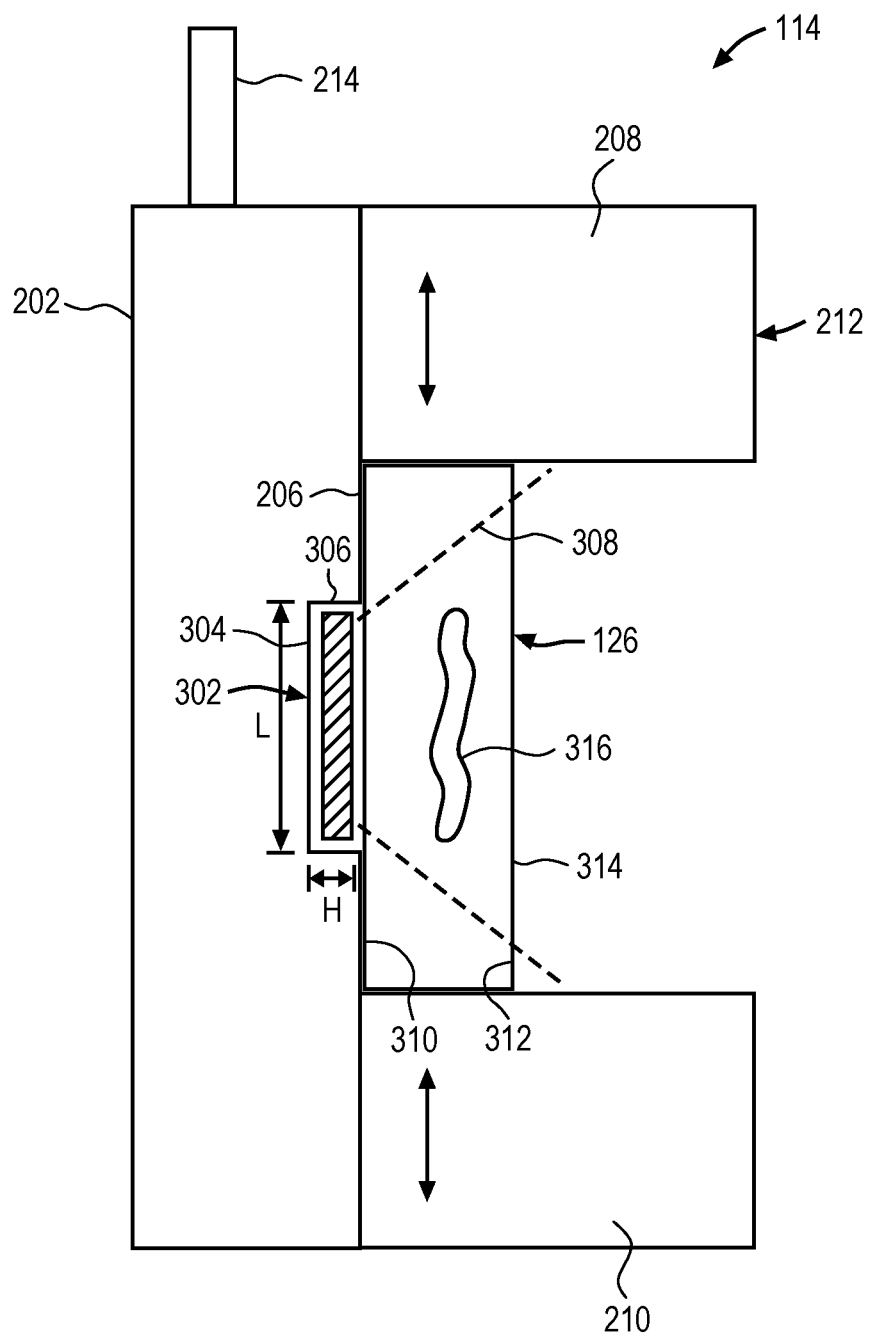
FIG. 3A illustrates another perspective view of the sample holder of FIG. 2.
Figure 3B:
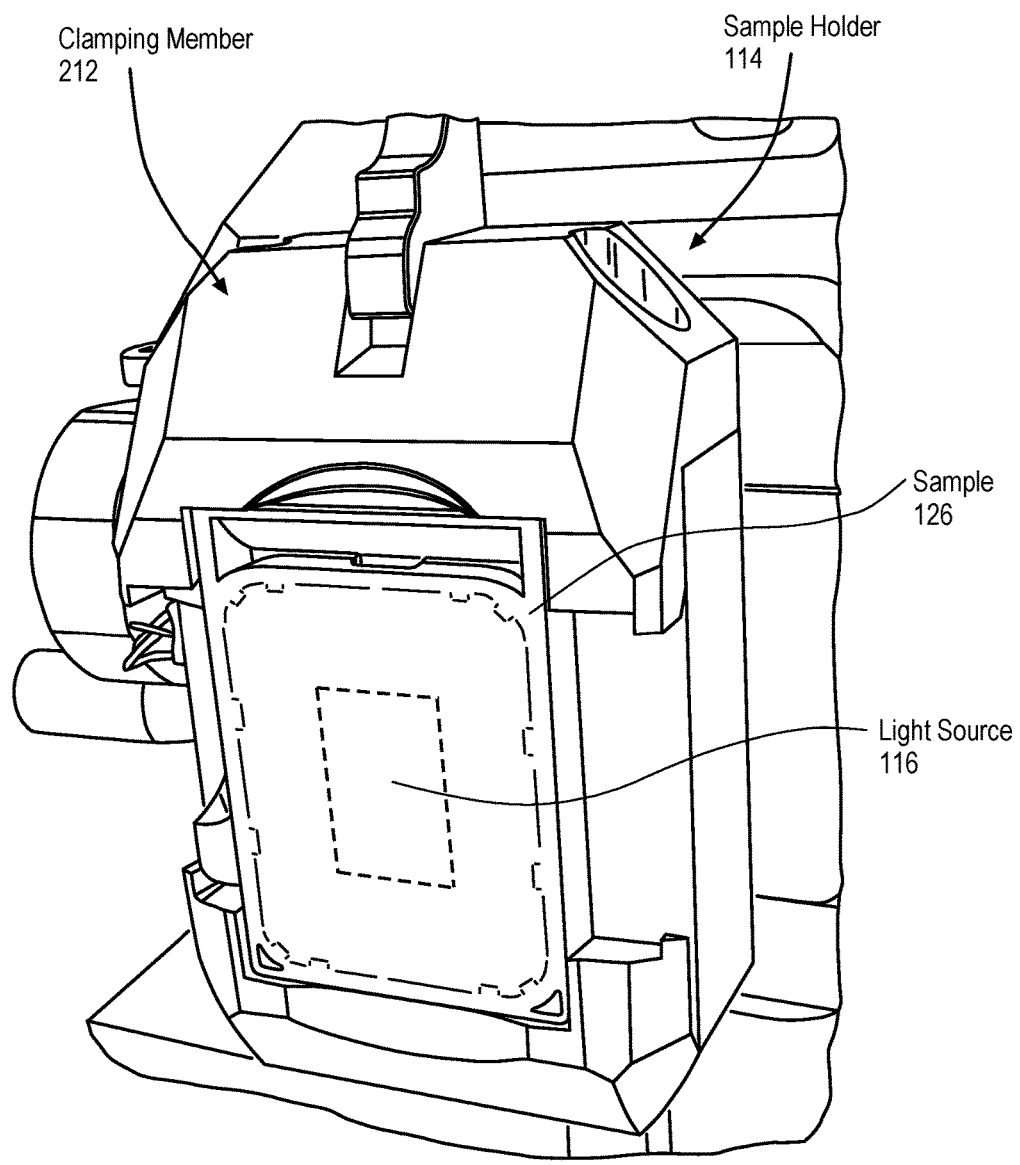
FIG. 3B illustrates a cross-sectional side view of the sample holder of FIG. 3A.
Figure 4:
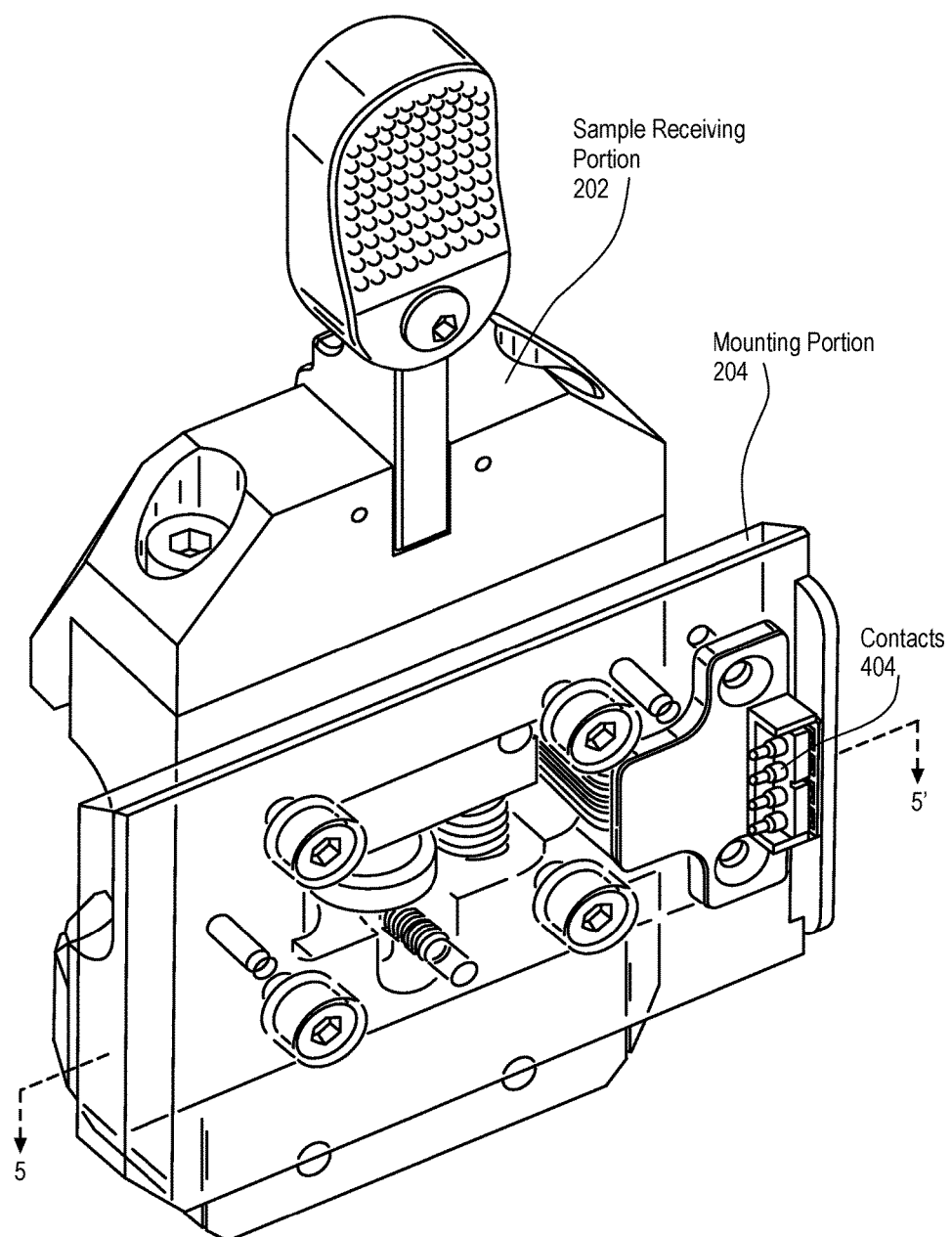
FIG. 4 illustrates a back side perspective view of the sample holder of FIG. 2.

Representatively, FIG. 3A is a cross-sectional side view, and FIG. 3B is a perspective view, of one embodiment of the sample holder of FIG. 2. FIG. 3A illustrates an embodiment in which light source 116 is positioned within a cavity 302 of the receiving surface 206 of sample receiving portion 202. In particular, cavity 302 is open to receiving surface 206, and formed by a sidewall 306 and a bottom wall 304 which are formed behind (or otherwise in a different plane than), receiving surface 206. Accordingly, when sample 126 is positioned on, and contacts, receiving surface 206, the light source 116 is considered behind sample 126. In other words, the light source 116 is between sample 116 and the bottom wall 302 of cavity 302. In this aspect, the light beam or ray 308 emitted by light source 116 is transmitted directly to, and contacts, the back side 310 of sample 116, and passes through sample 116, to the front side 312. By "directly" it is meant that the light beam or ray 308 is directed to, and reaches, the sample 116 without having to be redirected or refocused toward the sample 116, such as by an intervening optical element or reflective element. In addition, it should be recognized that because the light source 116 is a relatively low profile light source, such as an LED chip, light source 116 can rest against the bottom wall 302 of cavity 302 without extending beyond the plane of the receiving surface 206 upon which sample 126 rests. For example, in some embodiments, the height of sidewall 306 of cavity 302, and therefore the overall depth of cavity 302, can be substantially the same as a thickness of light source 116 (e.g., an LED chip), such that a planar, light emitting surface, of light source 116 is within a same plane, or substantially the same plane, as receiving surface 206. Said another way, cavity 302 is considered a relatively shallow cavity in that the length (l) of the bottom wall 304 is less than the height (h) of the side wall 306. Due to the dimensions of cavity 302 and light source 116, sample 126 can be positioned in close proximity to light source 116, and the associated light beam or ray 308, thus avoiding any unnecessary space or gap between the light source 116 and sample 126 through which light beam or ray 308 could leak through, and thereby result in less of the light beam or ray 308 reaching sample 126. It should further be understood that, in some embodiments, cavity 302 while being open to receiving surface 206, is closed to the back side of sample receiving portion 210, such that it does not extend entirely through portion 210. In this aspect, the entire light source 116 is considered closer to receiving surface 206, and in turn sample 126, than the back side of sample receiving portion 210. It is recognized, however, that while cavity 302 is illustrated and described as being formed in receiving surface 206, in some embodiments, it could be formed within any wall of the sample holder, for example a sidewall (e.g., a surface of member 208 or 210 facing the side of sample 126) so that it transmits light into a side of sample 126 that is not resting on surface 206.

In addition, in some embodiments, the surface area of light source 116 can be selected to cover a desired surface area of sample 126 so that maximum illumination of sample 126 is achieved. For example, light source 116 may have a surface area sufficient to illuminate an entire surface area of front side 312 of sample 126. Representatively, in one embodiment, light source 116 may have a substantially square or rectangular shaped light emitting surface area, and sample 126 may have a similar shape such that illumination of the sample 126, including the corners, is maximized. It should further be noted that the term "sample" is generally used to refer to, for example, a carrier 314 and a biological sample 316, such as a tissue, contained within the carrier 314. For example, the term "sample" could generally include a biological tissue 316 as well as the carrier 314, within which the biological tissue 316 is contained. The biological tissue 316 could be any type of biological material from a multicellular organ, for example, a bulk tissue and/or an aggregate of cells and cell products that together form a structural material having a particular function. For example, tissue 316 could be a tissue taken from the body, and which includes DNA, proteins, lipids, carbohydrates, fibers, connective tissue, or other types of tissue compounds or structures that can be highlighted, or otherwise made more visible, by the light source 116 shining there through. The carrier 316 could include a paraffin block, and in some cases a paraffin block positioned as well as a cassette within which it is positioned. For example, the cassette could be a plastic cassette that serves as a supporting structure for the paraffin during the process of embedding the biological tissue within the paraffin. In this aspect, illumination of sample 126, can be understood to mean that the biological tissue 316 (e.g., tissue), the carrier 314 (e.g., paraffin and/or cassette) and/or both the biological tissue 316 and carrier 314 are illuminated. The illumination of the entire sample 126 is illustrated in FIG. 3B.

Still further, in some embodiments, both an intensity or brightness and color or wavelength of the light output by the light source 116 may be controlled and modified depending on, for example, characteristics of the sample to be sliced. For example, in one embodiment, the light source 116 is an LED chip operable to output light of one, or a number of different colors. For example, the light source 116 may be an LED chip that includes a number of LEDs fabricated on, or otherwise electrically connected to, a semiconductor block or wafer (including a circuit). For example, the LED chip may include one or more LEDs that output different colored light, for example, light at wavelengths within a range of about 360 nanometers (nm) to about 425 nm (e.g., UV LEDs), from about 430 nm to about 505 nm (e.g., blue LEDs), from about 515 nm to about 570 nm (e.g., green LEDs), from about 585 nm to about 595 nm (e.g., yellow LEDs), 630 nm-660 nm (e.g., red LEDs) and from about 2200 Kelvin (K) to about 10000K (e.g., white LEDs). These different colored LEDS can be individually controlled, and in some cases their corresponding light output mixed, to produce the desired light color output. For example, two or more colored LEDs (e.g., primary LEDs) could be mixed to produce a single colored light output (e.g., a white light). Alternatively, an LED of a single color (e.g., white) could be operated alone while the other LEDs are turned off (e.g., primary LEDs), to achieve a desired color output. In addition, the intensity or brightness of one or more of the LEDs can be independently controlled or modified within a range of from about 50 millicandela (mcd) to about 15000 mcd. For example, an intensity or brightness of one LED (e.g., a red LED) could be increased while the intensity or brightness of another LED (e.g., a green LED) reduced, where a red output is desired. For example, an LED which outputs the desired color could be increased to a brightness or intensity of from about 1000 mcd to about 1500 mcd, while the intensity or brightness of an LED of a color that is not desired could be decreased to within a range below that of the desired colored LED, for example, a range of from about 50 mcd to about 1000 mcd. It should further be understood that although the adjustment of two exemplary LEDs is discussed, an intensity of brightness of more than two, for example, three, four, or more LEDs could be adjusted at the same time, consecutively or at different times to achieve a desired light output. In other words, they are all independently controlled therefore any combination of colors and/or intensity/brightness can be achieved depending on the desired output.

The intensity, brightness and/or color of the light output may be manually selected by the user, or automatically selected by a microtome controller depending upon, for example, a characteristic of the sample. For example, the sample characteristic may be a color or density of the tissue or features within the tissue (e.g., biological components such as DNA, proteins, lipids, carbohydrates, fibers, connective tissue, or the like), or a color or density of the medium in which the tissue is embedded (e.g., paraffin). In particular, the color or brightness of the light output by light source 116 can be modified to create more contrast between the tissue or characteristics of the tissue and the surrounding medium (e.g., paraffin). This may be achieved by, for example, modifying an intensity or brightness of one of the LEDs with respect to another of the LEDs so that a desired light output color is achieved. For example, where it is determined based on the sample that a blue light output would allow for better viewing of the sample, the intensity of a blue wavelength LED could be increased while the intensity of a red wavelength LED, green wavelength LED and/or yellow wavelength LED could be reduced, or turned off all together.

In addition, in still further embodiments, the characteristic of the sample may be a color of a cassette holding the paraffin embedded tissue. For example, in one embodiment, the cassette may be a cassette having a particular color (e.g., red, orange, yellow, blue, green, purple, pink, brown, etc.). In this aspect, when the light source 116 emits a white light through openings (or grills) in the cassette, the paraffin surrounding the tissue may appear the color of the cassette. For, example, the cassette may be a red cassette from the Tissue-Tek® III Uni-Cassette® System available from Sakura Finetek Europe B.V., which has grills or openings to allow for fluid exchange during tissue processing operations. When light source 116 emits a white light through the sample, the red color of the cassette may cause the paraffin to appear red to the viewer. To compensate for this color change due to the color of the cassette, the red, green and/or blue intensity of the white light can be individually controlled to decrease the intensity of the color of the light reflected by the red cassette, so that the paraffin appears white again.

Figure 23:
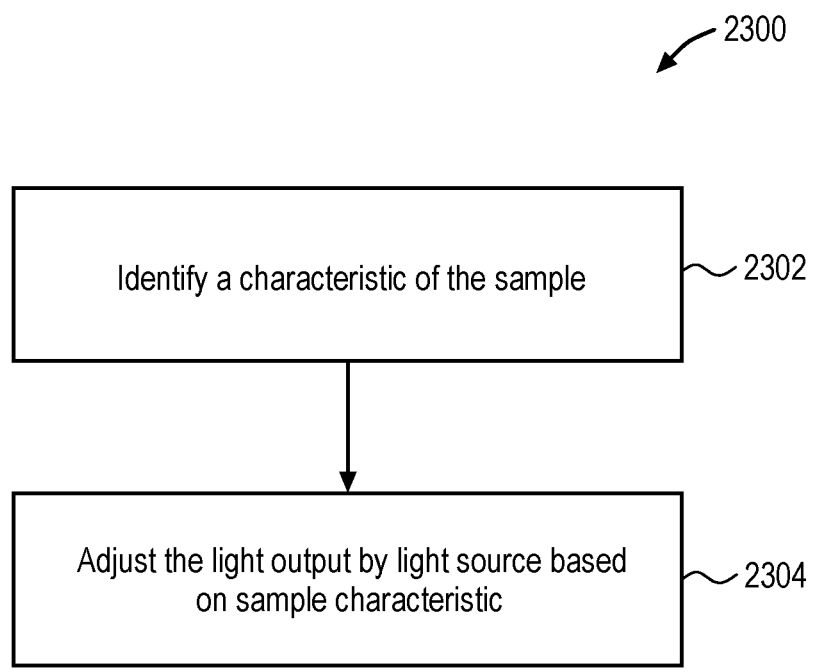
FIG. 23 illustrates a block diagram of one embodiment of a process for controlling a light source based on a sample characteristic.

One exemplary process for controlling the output of the light source 116 based on a characteristic of the sample is illustrated in FIG. 23. Representatively, in one embodiment, process 2300 includes the operation of determining a characteristic of the sample (block 2302). The characteristic of the sample may be, for example, a color or density of the tissue or features within the tissue, a color or density of the medium in which the tissue is embedded (e.g., paraffin), a color of the cassette within which the paraffin embedded tissue is held, or in some cases, a color of the paraffin. This characteristic may be determined manually (e.g., a user observing a characteristic of the sample), or automatically (e.g., a scanner reading an identifier associated with the sample that contains the information about the sample characteristic). Based on this information, the light output by light source 116 may then be adjusted or controlled to illuminate the sample as desired. For example, as previously discussed, in an embodiment where the cassette is red (or another color), the red, green and/or blue intensity of the white light can be individually controlled to decrease the intensity of the color of the light reflected by the red cassette, so that the paraffin appears white again.

Figure 5:
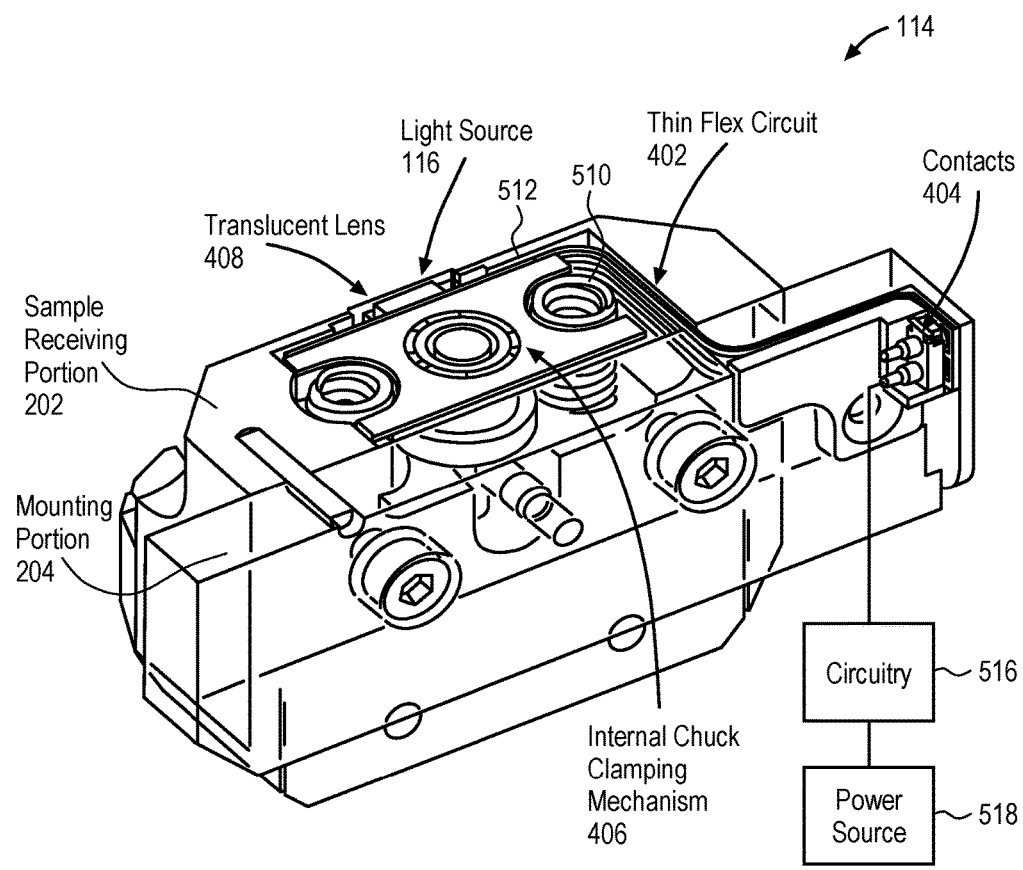
FIG. 5 illustrates a cross-sectional bottom perspective view of the sample holder of FIG. 4, along line 5-5'.

Returning now to further aspects of light source 116, light source 116 may be electrically connected to a microtome, and its associated electronic components and/or a power source, by circuitry within sample holder 114. Representatively, as can be seen from the back side view of sample holder 114 illustrated in FIG. 4, and the bottom section view of FIG. 4, along line 5-5' as illustrated in FIG. 5, sample receiving portion 202 of sample holder 114 is mounted to, or otherwise includes, mounting portion 204. Mounting portion 204 may be any type of mounting member suitable for mounting, or otherwise connecting, sample holder 114 (e.g., the chuck) to the microtome, as previously discussed.

More specifically, as seen from the cross-sectional view of FIG. 5, sample holder 114 includes an internal chuck clamping member 406. Internal chuck clamping member 406 may include biasing members 510 (e.g., springs) and be part of clamping member 212, for example, connected to clamping portions 208, 210 (see FIG. 2) to facilitate clamping of the sample within receiving portion 202. The clamping member 406 is positioned within a channel 512 formed within sample receiving portion 202, and behind light source 116. In this aspect, clamping member 406 may be considered directly behind light source 116. The region of channel 512 between light source 116 and clamping member 406 may be used to support a flexible circuit 402 that electrically connects light source 116 to a source of power. For example, flexible circuit 402 may be positioned over the portion of clamping member 406 facing light source 116. Flexible circuit 402 may be electrically connected at one side to light source 116 by electrical contacts (not shown) associated with light source 116. The flexible circuit 402 may be electrically connected at another side to electrical contacts 404 of mounting portion 204, which electrically connect to circuitry 516 and a power source 518. Circuitry 516 may be any type of circuitry operable to process, control, and/or execute instructions, a processing protocol, or the like used for operation of a microtome (e.g., a light source operation). Power source 518 may be any type of power source operable to provide power to the microtome components (e.g., the light source), for example, a generator, AC power supply, battery power or the like. In this aspect, light source 116 may be electrically connected to electrical contacts 404 of mounting portion 204, and in turn receive instructions and/or power to operate the light source 116, via flexible circuit 402. It is to be understood that although a flexible circuit is illustrated, light source 116 may be electrically connected to electrical contacts 404 in any suitable matter (e.g., wires or the like).

The mounting portion 204 of sample holder 114 may then be mounted to a portion of the microtome (e.g., front portion 108 of housing 102) with corresponding electrical contacts or terminals that make contact with electrical contacts 404 within mounting portion 204. For example, mounting portion 204 may have a mating portion (e.g., groove, protrusion, track, channel or the like) complementary to a mating portion of the device it is to be mounted to (e.g., a microtome) such that it can, in one aspect, be mounted to the device, and in another aspect, removed from the device. The corresponding electrical contacts or terminals of the microtome may be associated with a power source (e.g., an outlet, a battery, a generator or the like) or other circuitry used to provide power to and/or control an operation of light source 116 as previously discussed, more specifically each LED making up light source 116 individually. In this aspect, because sample holder 114 is not hard wired into the microtome itself, it can be removed and mounted to any microtome having a corresponding electrical contact suitable for providing power and/or signals to light source 116.

FIG. 6, FIG. 7, FIG. 8 and FIG. 9 illustrate schematic views of various energy harvesting mechanisms that may, in one embodiment, be used to supply power to light source 116, or any other electronic components associated with sample holder 114 (e.g., an alarm). Representatively, in embodiments where microtome 100 is a manual microtome, there is no active power source (e.g., electrical current) associated with the microtome to, for example, drive movement of the sample holder 114 during a slicing operation. Rather, rotation of the hand wheel mechanically drives, for example, the up and down movement of sample holder 114 with respect to the cutting mechanism to slice the sample. Similarly, because the microtome is completely manual, there is no power source for operation of light source 116. Therefore, in one embodiment, microtome 100 further includes an energy harvesting mechanism for generating power (in the absence of electrical energy), that can be used for operation of light source 116, and in some cases, can be stored for later operation of light source 116. The energy harvesting mechanism may be any type of system capable of converting one form of energy (e.g., mechanical, motive or solar energy) into an electrical energy that can be used to power light source 116, and any other components associated with the microtome that may require an electrical input (e.g., an alarm).

Figure 6:
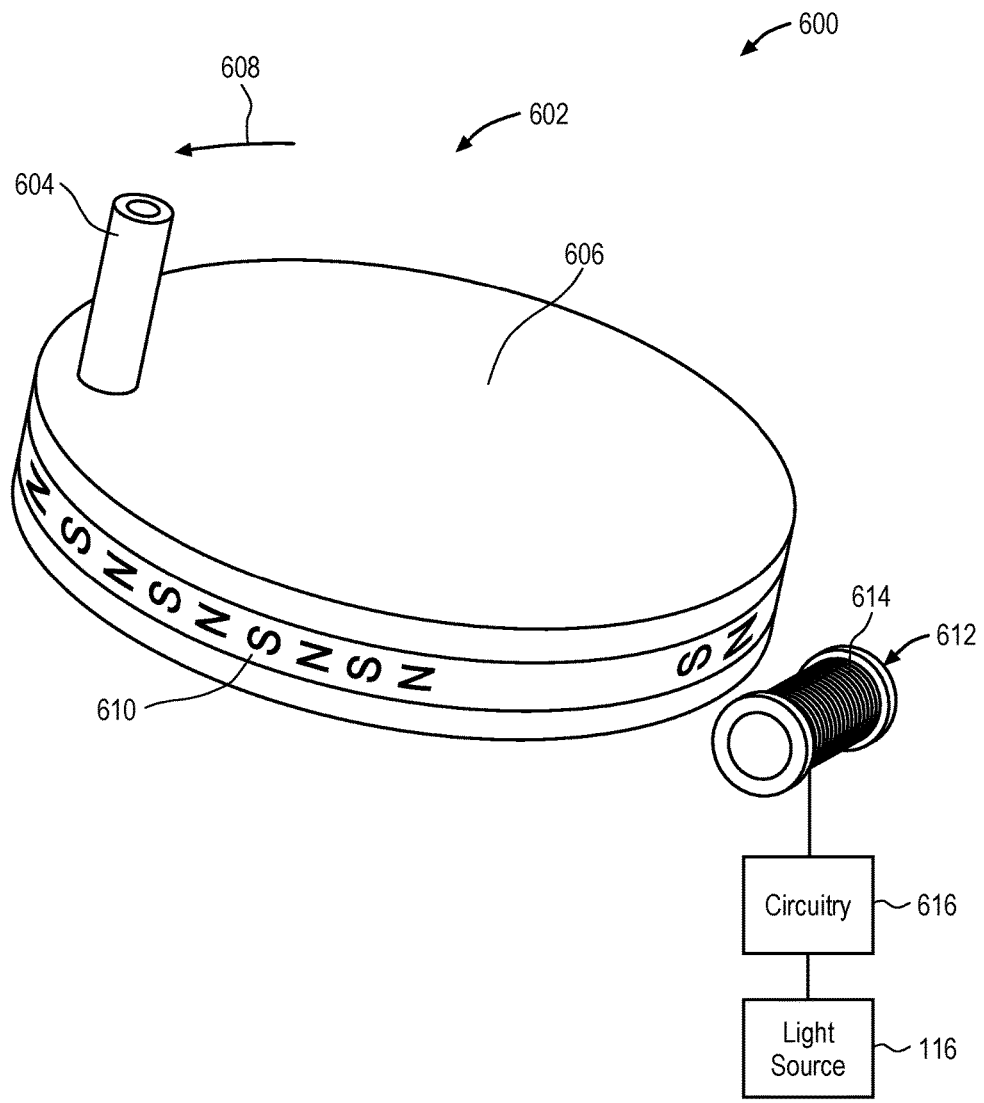
FIG. 6 illustrates a schematic diagram of one embodiment of a generator associated with a sample sectioning device.

Representatively, FIG. 6 illustrates a schematic view of one embodiment where the energy harvesting mechanism is a generator 600 that can generate electricity from the rotation of a hand wheel 602 associated with the microtome (see also hand wheel 118 previously discussed in reference to FIG. 1). Representatively, the hand wheel 602 may include a handle 604 connected to disc 606 that rotates as shown by arrow 608 upon rotation of handle 604. To facilitate energy generation, the disc 606 may include a magnetic strip 610 arranged in series along its outer edge and a rotating magnetic core 612 that is magnetically coupled with disc 606. The magnetic core 612 may, in turn, include coils 614 within which an electric current can be generated when magnetic core 612 is rotated with respect to magnetic strip 610. This electric current or voltage is, in turn, transmitted from coils 614 to circuitry 616 (e.g., processing circuitry or a controller) and ultimately to light source 116 (e.g., by the electrical contacts 404 of mounting portion that are connected to flexible circuit 402). In this aspect, generator 600 uses the rotation of hand wheel 602 to generate an electric current or voltage that can then be carried to light source 116 via circuitry as previously discussed. It should be understood that since, in this embodiment, disc 606 must be rotating to generate the electric current, in some embodiments, a storage module may further be provided so that the electricity can be stored and used at a later time (e.g., on demand such as by pressing a button or operating a switch), without having to rotate disc 606.

Figure 7:
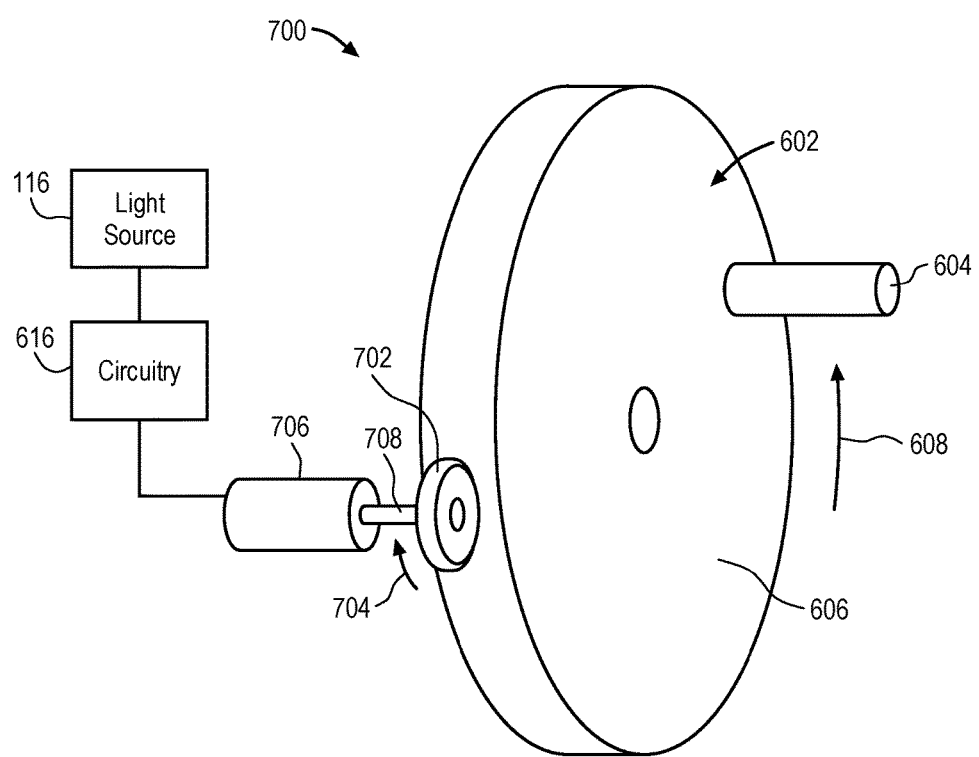
FIG. 7 illustrates a schematic diagram of another embodiment of a generator associated with a sample sectioning device.

FIG. 7 illustrates a schematic view of another embodiment of a microtome generator. In this embodiment, generator 700 includes a microtome hand wheel 602 having a handle 604 coupled to a disc 606. Handle 604 can be used to rotate disc 606 as shown by arrow 608 to actuate, for example, a cutting operation, as previously discussed. In this embodiment, however, disc 606 is coupled to a smaller wheel 702 that is coupled to a stepper motor 706 to generate an electric current. In particular, rotation of disc 606 (such as by rotation of handle 604) causes a rotation of smaller wheel 702 as shown by arrow 704, which is coupled to stepper motor 706 by axle 708, and in turn, drives stepper motor 706 and generates an electric current or voltage. The stepper motor 706 may be coupled to circuitry 616 which can be used to transmit the generated current or voltage to light source 116 to provide power to light source 116. Similar to generator 600, generator 700 may also be coupled to a storage module that can store the electrical current or voltage, so that it can be used at a later time to power light source 116.

Figure 8:
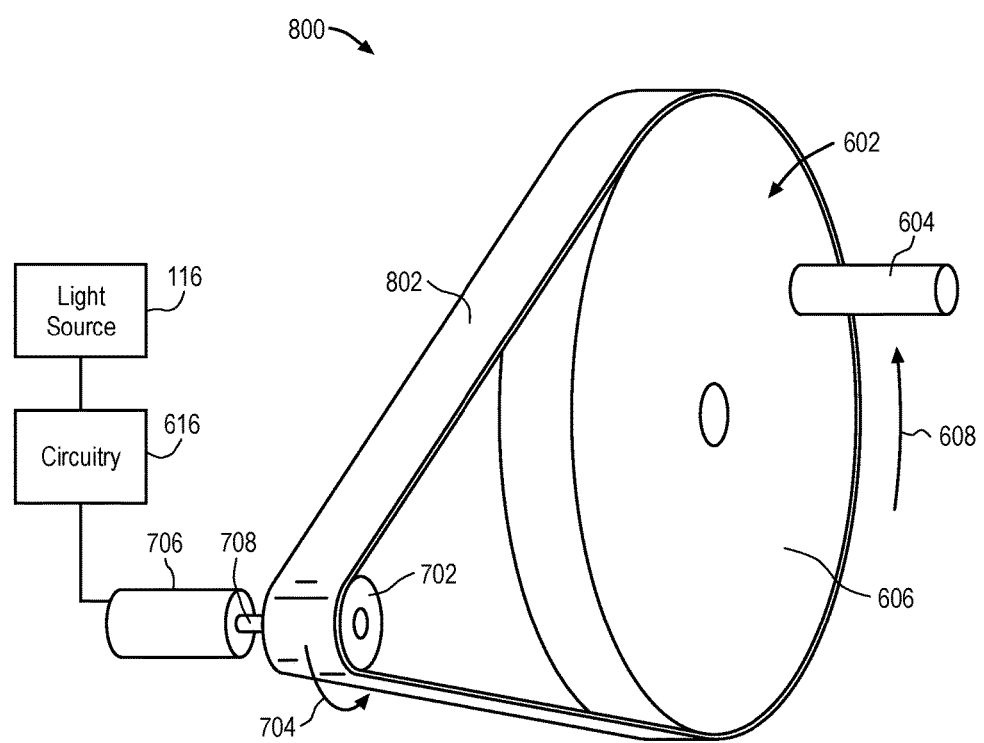
FIG. 8 illustrates a schematic diagram of another embodiment of a generator associated with a sample sectioning device.

FIG. 8 illustrates a schematic view of another embodiment of a microtome generator. In this embodiment, generator 800 is substantially similar to generator 700 described in reference to FIG. 7, except in this embodiment, a belt 802 is coupled to the smaller wheel 702 to rotate smaller wheel 702 when disc 602 is rotated (e.g., using handle 604), and generate electricity using stepper motor 706. In particular, belt 802 encircles disc 606 and the smaller wheel 702. Rotation of disc 606 causes belt 802 to rotate smaller wheel 702, and in turn, stepper motor 706 generates a voltage that can be used to power light source 116. For example, the stepper motor 706 is coupled to circuitry 616 (and in some cases storage), which facilitates transmission of the electric current or voltage to light source 116, as previously discussed.

Figure 9:
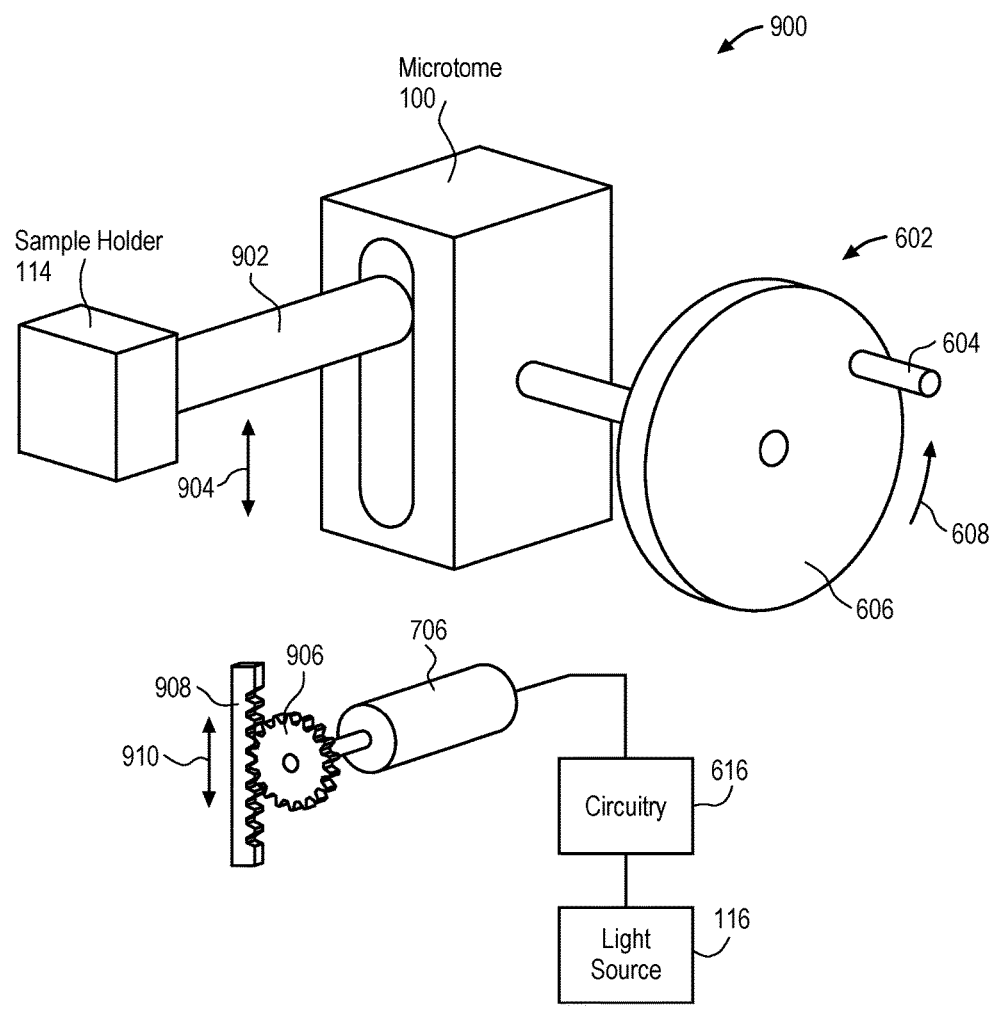
FIG. 9 illustrates a schematic diagram of another embodiment of a generator associated with a sample sectioning device.

FIG. 9 illustrates a schematic view of another embodiment of a microtome generator. In this embodiment, generator 900 includes a rack and pinion arrangement that is used to generate an electric current or voltage using a stepper motor. In particular, rotation of hand wheel 602 as previously discussed, causes a shaft 902 associated with sample holder 114 to move up and down as illustrated by arrow 904.

Shaft 902 contacts rack 908, which is positioned near shaft 902, causing rack 908 to also move up and down, as illustrated by arrow 910. Rack 908 is coupled to pinion 906 of stepper motor 706. The movement of rack 908, therefore, in turn, causes pinion 906 to rotate, and drive stepper motor 706 associated with pinion 906, which in turn, generates an electric current or voltage. The stepper motor 706 is coupled to circuitry 616 (and in some cases storage), which facilitates transmission of the electric current or voltage to light source 116, as previously discussed.

Figure 10:
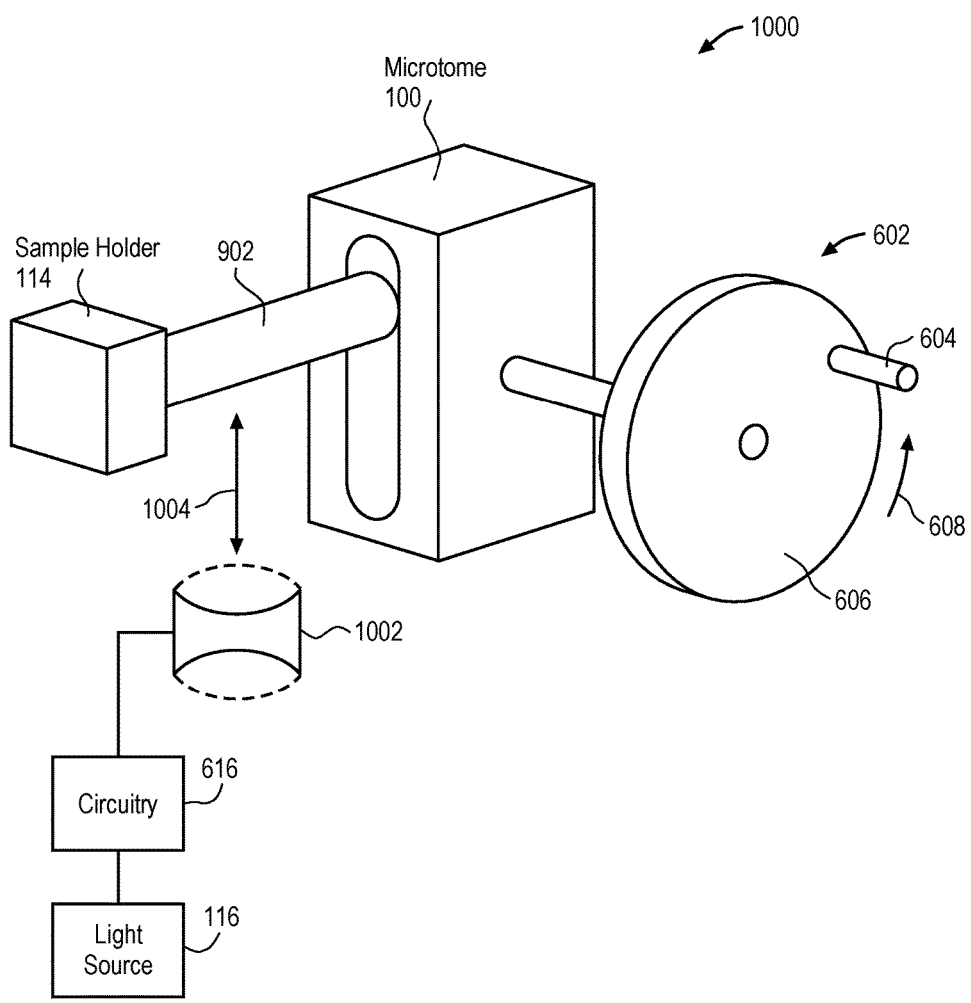
FIG. 10 illustrates a schematic diagram of another embodiment of a generator associated with a sample sectioning device.

FIG. 10 illustrates a schematic view of another embodiment of a microtome generator. In this embodiment, generator 1000 includes piezoelectric material 1002 that is used to generate an electric current or voltage. Representatively, in this embodiment, generator 1000 includes a piezoelectric material 1002 which is either compressed or expanded by shaft 902 as it moves up and down as illustrated by arrow 1004, as previously discussed. This, in turn, cause the piezoelectric material 1002 to generate an electrical charge corresponding to an electric current or voltage. The piezoelectric material 1002 is coupled to circuitry 616 (and in some cases storage), which facilitates transmission of the electric current or voltage to light source 116, as previously discussed.

It should be understood that in any of the previously discussed embodiments, the voltage or electric current produced by the generator can be used to power any component of the microtome so that, for example, a cutting operation, a processing protocol or the like, may be completed. For example, in one embodiment, the electric current can be used to turn on/off light source 116, modify a brightness or intensity of light source 116, or modify a color or wavelength of light source 116, as previously discussed. In addition, it should be understood that in embodiments where the light source 116 includes a number of LEDs, the voltage or electric current can be used to operate or otherwise control (e.g., turn on/off, modify a brightness or intensity, or modify a color or wavelength) each of the LEDs individually. In addition, in some embodiments, microtome 100 further includes a storage module, for example a battery or capacitor, that can be used to store the voltage produced by the generator and used to provide power to light source 116 when the hand wheel is not being rotated. In this aspect, light source 116 can be used not only during a cutting operation in which hand wheel is being rotated, but also when hand wheel is not being rotated. In addition, the voltage can be used to provide power to other electronic components that may be associated with the microtome. For example, the electronic component may be an alarm (see alarm 1116 of FIG. 11) that lights up, vibrates or makes a noise when the hand wheel is being rotated to alert a user that a cutting operation is being performed. In this aspect, an alarm that could typically not be used with a manual microtome because there is no power source, can now be used to alert the user. It should be recognized that although the alarm is described as being used to alert the user of a cutting operation, it may be used to alert the user of any information desired during operation of a microtome (e.g., completion of a cutting cycle, presence/absence of a sample, low power, etc.).

Figure 11:
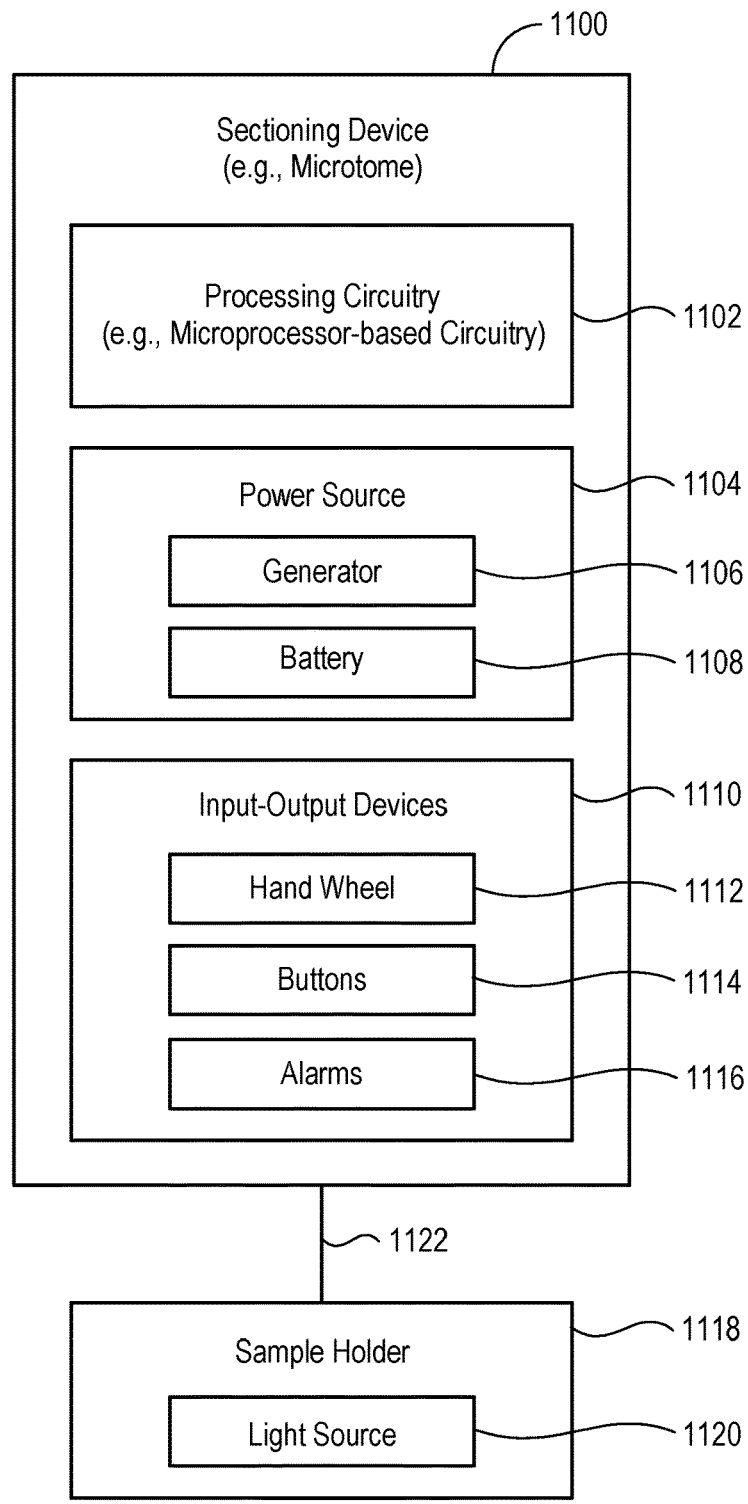

As previously discussed, the slicing operation may proceed manually through user interaction with the system, or in some cases, automatically. FIG. 11 illustrates a schematic block diagram of one embodiment of a microtome including a hand wheel, a generator and processing circuitry for controlling an operation of the light source associated with the sample holder. Representatively, device 1100 may include processing circuitry 1102, a power source 1104 and input-output devices 1110 and be associated with sample holder 1118. Processing circuitry 1102 may be used to control the operation of a light source 1120 associated with sample holder 1118, or other electronic components associated with device 1100 (e.g., an alarm). Processing circuitry 1102 may be based on a processor such as a microprocessor and other suitable integrated circuits. With one suitable arrangement, processing circuitry 1102 may be used to run, for example, software on device 1100 which controls an operation of light source 1120 (e.g., on/off, a brightness or color).

Input-output devices 1110 may be used to allow data and/or instructions to be supplied to device 1100 and to allow data to be provided from device 1100 to external devices. A hand wheel 1112, buttons 1114 and alarm 1116 are all examples of input-output devices 1110. A user can control the operation of device 1100 by supplying commands through user input devices such as hand wheel 1112 and buttons 1114. In some embodiments, an optional display and audio devices may be provided, which could include liquid-crystal display (LCD) screens or other screens, light-emitting diodes (LEDs), and other components that present visual information and status data. Display and audio devices may also include audio equipment such as speakers and other devices for creating sound. Display and audio devices may contain audio-video interface equipment such as jacks and other connectors for external headphones and monitors.

Device 1100 may further include power source 1104 for supplying power to electronic components associated with device 1100 (e.g., a light source or alarm). Power source 1104 may include a generator 1106 that, for example, uses the rotation of hand wheel 1112 to generate electricity, as previously discussed. Power source 1104 may further include a battery 1108 or other device such as a capacitor that can store electrical energy (e.g., energy generated by the generator) for later use. In addition, in still further embodiments, power source 1104 may include a wall mounted plug-in power supply, for example, in the case of an automated microtome.

Device 1100 can communicate with external devices, such as sample holder 1118 as shown by path 1122. Path 1122 may include a wired or wireless paths (e.g., flexible circuit 402 described in FIG. 4-FIG. 5). Sample holder 1118 may include a light source 1120, and be substantially similar to sample holder 114 and light source 116 previously discussed in reference to FIG. 1-5. In this aspect, an electric current generated by, for example, generator 1106 may be used to power light source 1120 and processing circuitry 1102 may be used to control an operation of light source 1120 (e.g., control a brightness or color).

Figure 12:
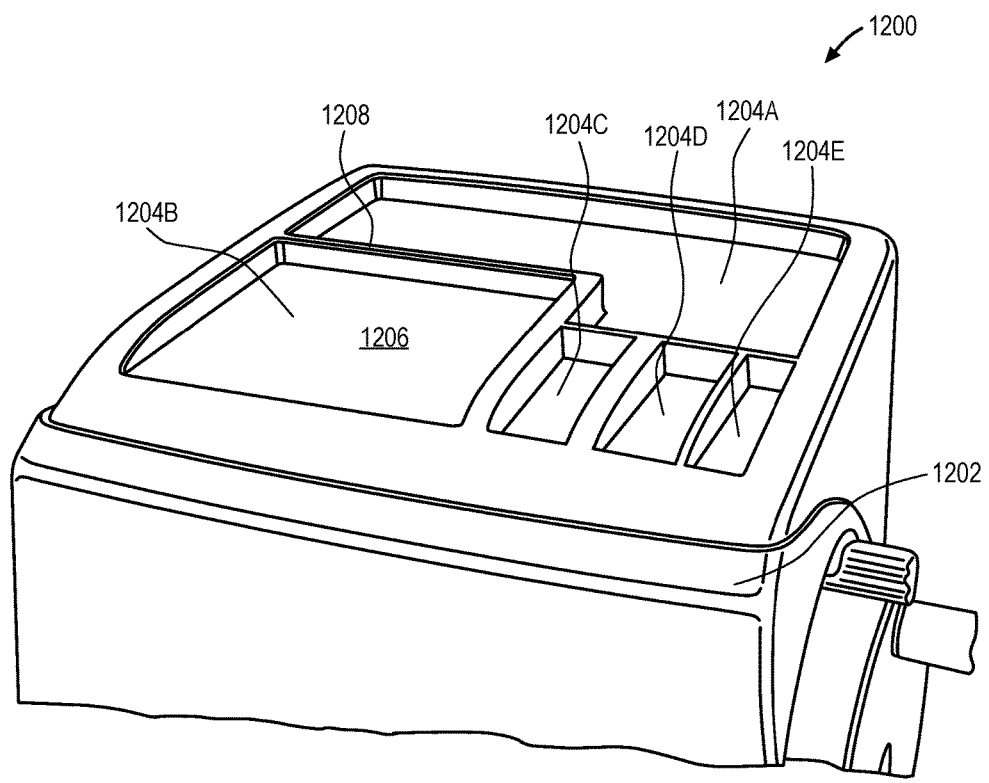
FIG. 12 illustrates a perspective view of one embodiment of a microtome storage member.
Figure 13:
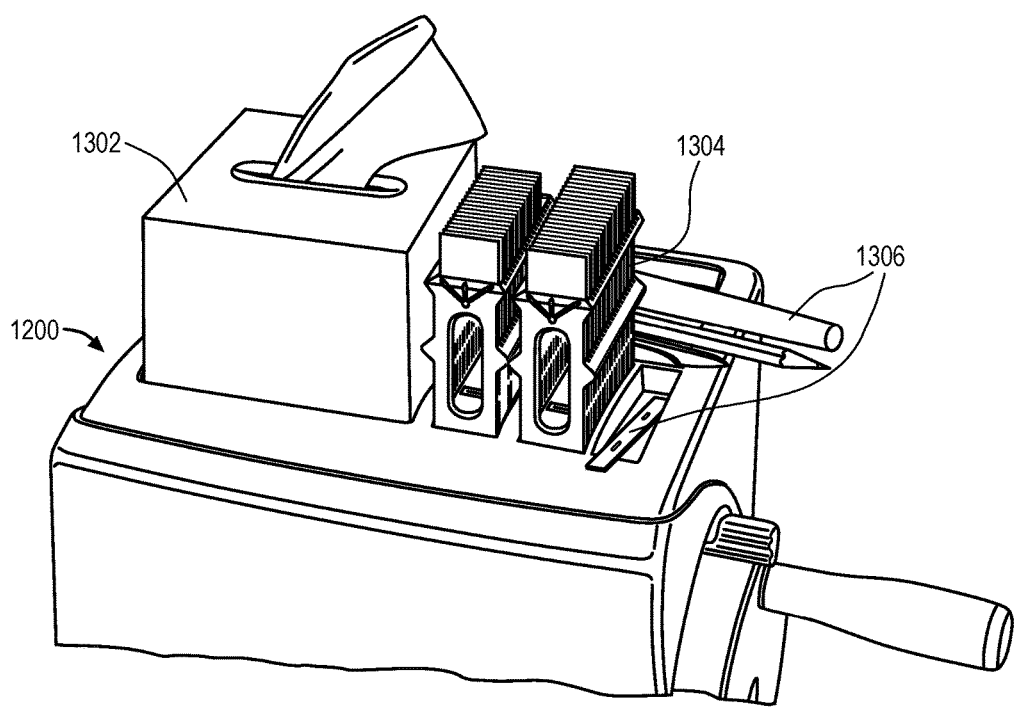
FIG. 13 illustrates another perspective view of the microtome storage member of FIG. 12.
Figure 14:
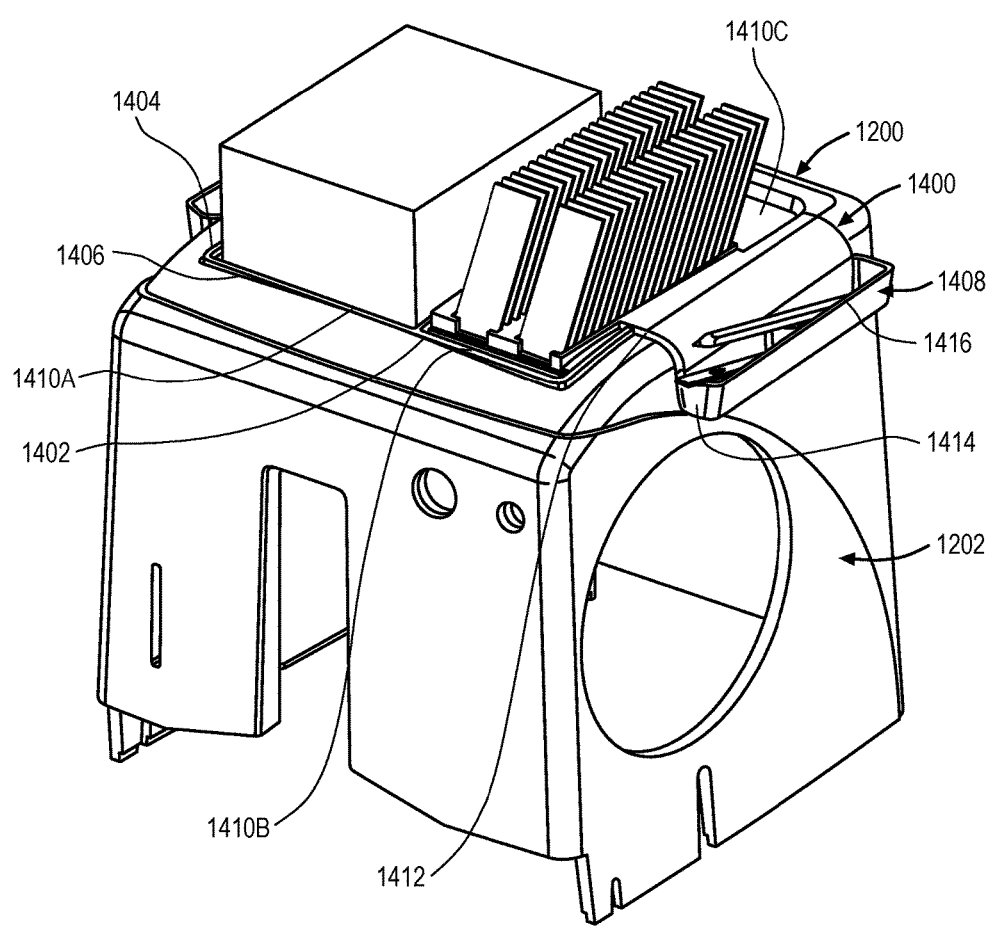
FIG. 14 illustrates a perspective view of another embodiment of a microtome storage member.

FIG. 12-FIG. 16B illustrate perspective views of various embodiments of a storage member associated with a sample sectioning device such as a microtome. Representatively, FIG. 12 shows storage member 1200 that is designed to store various sample sectioning device accessories on microtome 1202. Microtome 1202, may for example, be substantially similar to microtome 100 previously discussed in reference to FIG. 1, which is coupled to a sectioning assembly 110 (e.g., chuck), therefore the specific features previously discussed in reference to FIG. 1 will be omitted here. Instead, the various aspects of the associated storage member 1200 will now be discussed. Representatively, in one embodiment, storage member 1200 may be integrally formed within a top portion of microtome 1202. For example, storage member 1200 may be part of, and inseparable from, the top portion 106 of housing 102 previously discussed in reference to FIG. 1. Representatively, storage member 1200 may include recessed regions 1204A, 1204B, 1204C, 1204D and 1204E that are formed within the top portion (or wall) of the housing of microtome 1202. Recessed regions 1204A-1204E may have any size and shape suitable for receiving and holding microtome accessories therein as shown in FIG. 13. Representatively, recessed regions 1204A-1204E may have square or rectangular profiles and be sized to accommodate microtome accessories such as a tissue box 1302, slide carrier 1304, elongated instruments 1306 or the like can be positioned on top of microtome and stored there without falling off. For example, each of recessed regions 1204A-1204E may include a base portion 1206 upon which the desired microtome accessory can rest, and one or more sidewall(s) 1208 which surrounds the base portion 1206, and separate one recessed region from another recessed region. Each of the base portion 1206 and sidewall(s) 1208 of storage member 1200 may be formed of the same material as the microtome housing (e.g. a plastic or the like). In some cases, a portion of the recessed regions 1204A-1204E (e.g., base portion 1206) may be texturized, or otherwise have a non-smooth surface or include a texturized mat, to help hold the desired microtome accessory therein.

FIG. 14-FIG. 16B illustrate perspective views of other embodiments of a storage member than can be used in addition to, or instead of, storage member 1200. It should be noted that for ease of illustration, the various interior components of the microtome are omitted in FIG. 14-FIG. 16B, however, could also be present. Representatively, storage member 1400 in this embodiment, is a tray like structure that is separate from the microtome housing and is dimensioned to rest on top of microtome 1202, for example, within the recessed regions or cavities formed by storage member 1200 previously discussed in reference to FIG. 12-FIG. 13. Storage member 1400 can rest on top of microtome 1202, and can also be removed from microtome 1202. In this aspect, the contents of storage member 1400 can be moved to a different location than microtome 1202 (e.g., off to the side of microtome), while still maintaining the same arrangement and/or position so that the user can easily locate each accessory.

In one embodiment, storage member 1400 may have a receiving member 1402, that is designed to store microtome accessories, and a support member 1408 that is designed to help hold the storage member 1400 on microtome 1202, and may also be used for storage. In this aspect, receiving member 1402 may include a storage surface 1404 and a mating surface 1406. Storage surface 1404 may be a top side of receiving member 1402 (e.g., a side that faces away from the microtome) and include various recessed regions or cavities 1410A, 1410B, 1410C dimensioned to retain microtome accessories (e.g., tissue box, slide carrier, slides, elongated instruments or the like). Mating surface 1406 is formed by an opposite side of receiving member 1402 and is dimensioned to mate with recesses formed on a top portion of microtome 1202 (e.g., recessed regions 1204A-1204E). For example, mating surface 1406 may include protruding portions that are complimentary to recesses or cavities along the top portion of microtome 1202 (e.g., within storage member 1200) and fit within the cavities to hold storage member 1400 in place.

Support member 1408 may extend from receiving member 1402 and overlap a side of microtome 1202 as shown to help hold storage member 1400 in place. In particular, support member 1408 may include a first portion 1412 that is substantially flat, planar or curved, and extends from an edge of receiving member 1402 (e.g., horizontally), and a second portion 1414 that is at an angle to first portion 1412 such that it extends in a downward direction (e.g., vertically) along the side of microtome 1202. In other words, second portion 1414 is at an angle with respect to first portion 1412. For example, second portion 1414 may be considered to curve around an edge of microtome 1202 and downward from first portion 1412. Support member 1408 may further include a cavity or channel 1416 that can also be used to store microtome accessories along a side of microtome 1202 as shown. The cavity or channel 1416 may have an elongated profile and extend along a portion of the side of microtome 1202.

Figure 15A:
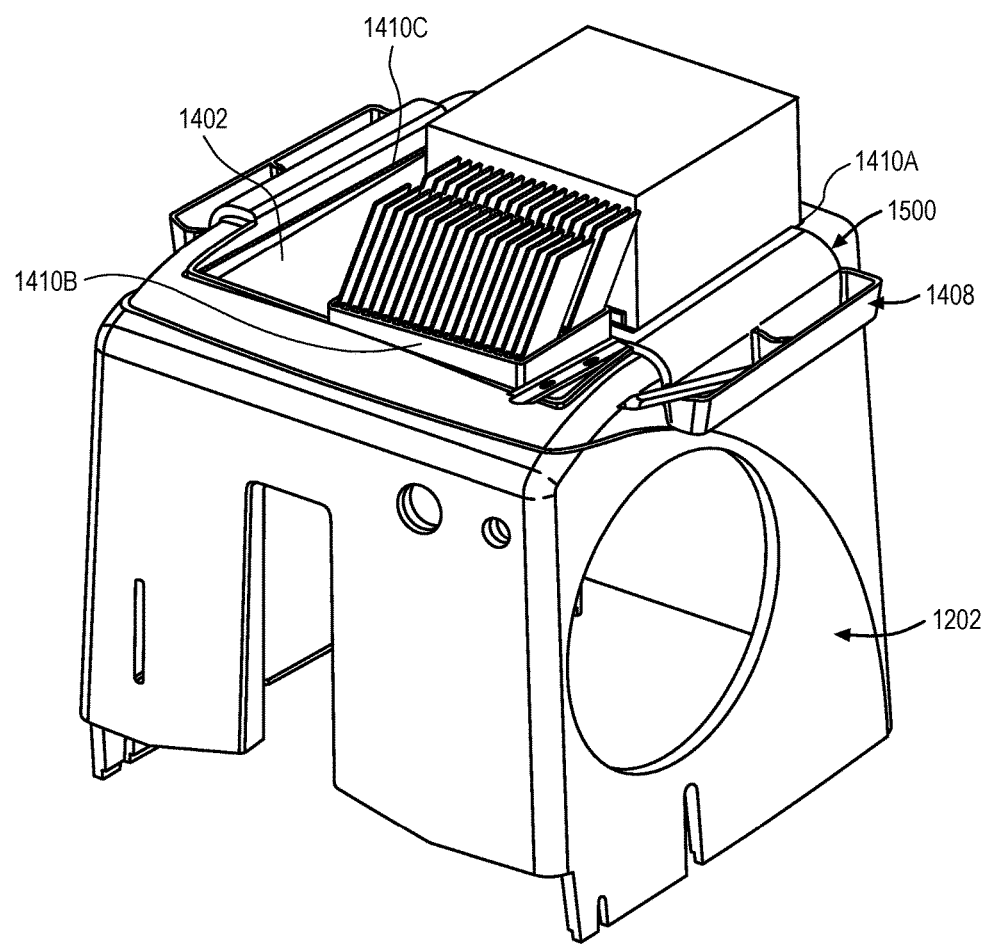
FIG. 15A illustrates a perspective view of another embodiment of a microtome storage member.
Figure 15B:
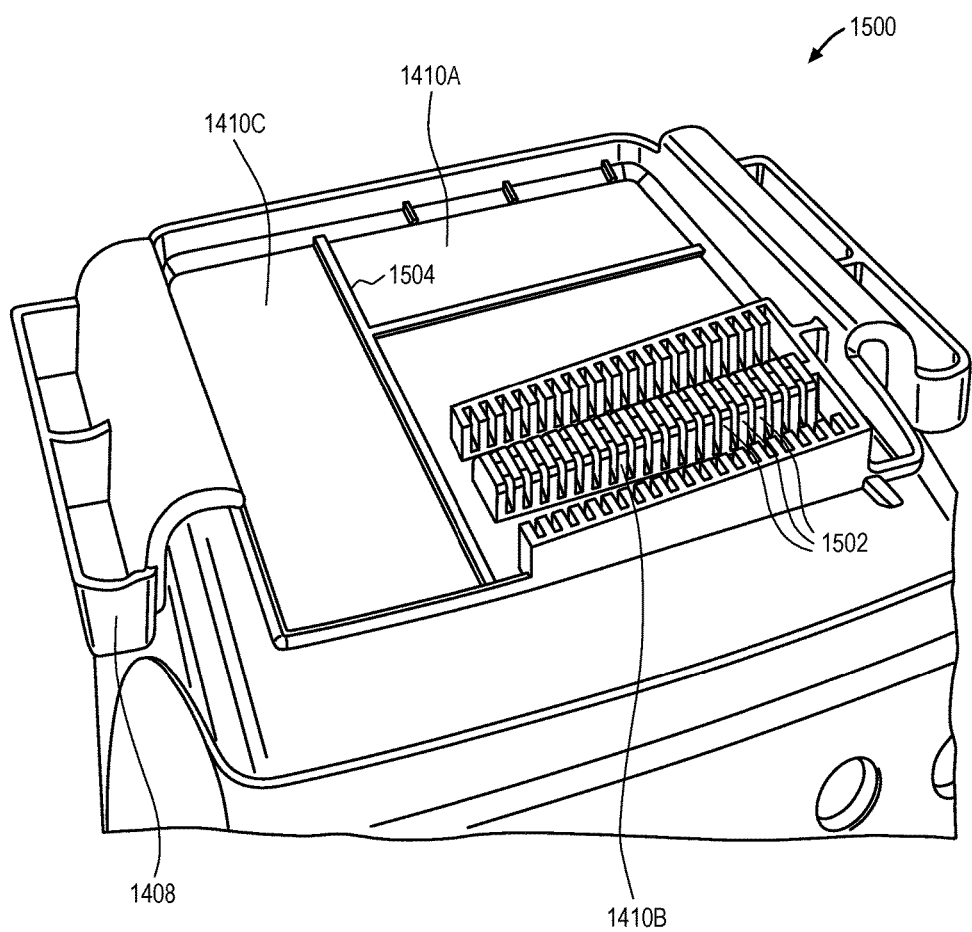
FIG. 15B illustrates a perspective view of the microtome storage member of FIG. 15A.

FIG. 15A illustrates a perspective view of another embodiment of a storage member. Storage member 1500 shown in FIG. 15A is substantially similar to storage member 1400, except in this embodiment, the cavities 1410A-1410C are arranged differently along receiving member 1402. FIG. 15B illustrates a perspective view of storage member 1500 with the microtome accessories removed so that cavities 1410A-1410C can be more clearly seen. In particular, from this view, it can be seen, for example, that recessed region or cavity 1410B includes a number of slots 1502, which are dimensioned to receive and hold a microscope slide within cavity 1410B. Representatively, the slots 1502 may have walls, which are evenly spaced from one another and form cavities (about the distance of a slide) dimensioned to hold the microscope slides next to each other, on their sides, and in some cases, at a slight angle. Cavities 1410A and 1410C may further be formed by recessed regions defined by side walls 1504.

Figure 16A:
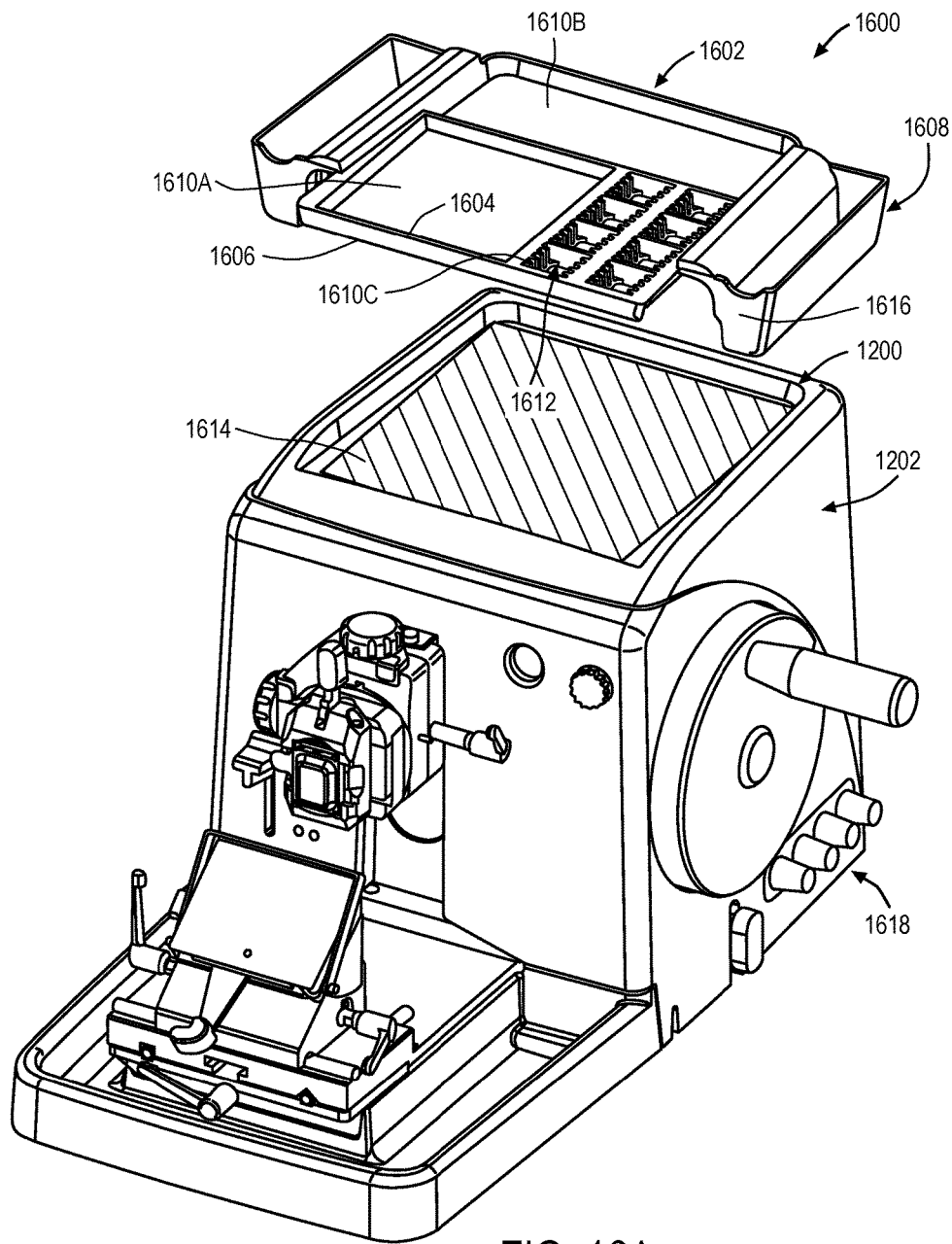
FIG. 16A illustrates a perspective view of another embodiment of a microtome storage member.
Figure 16B:
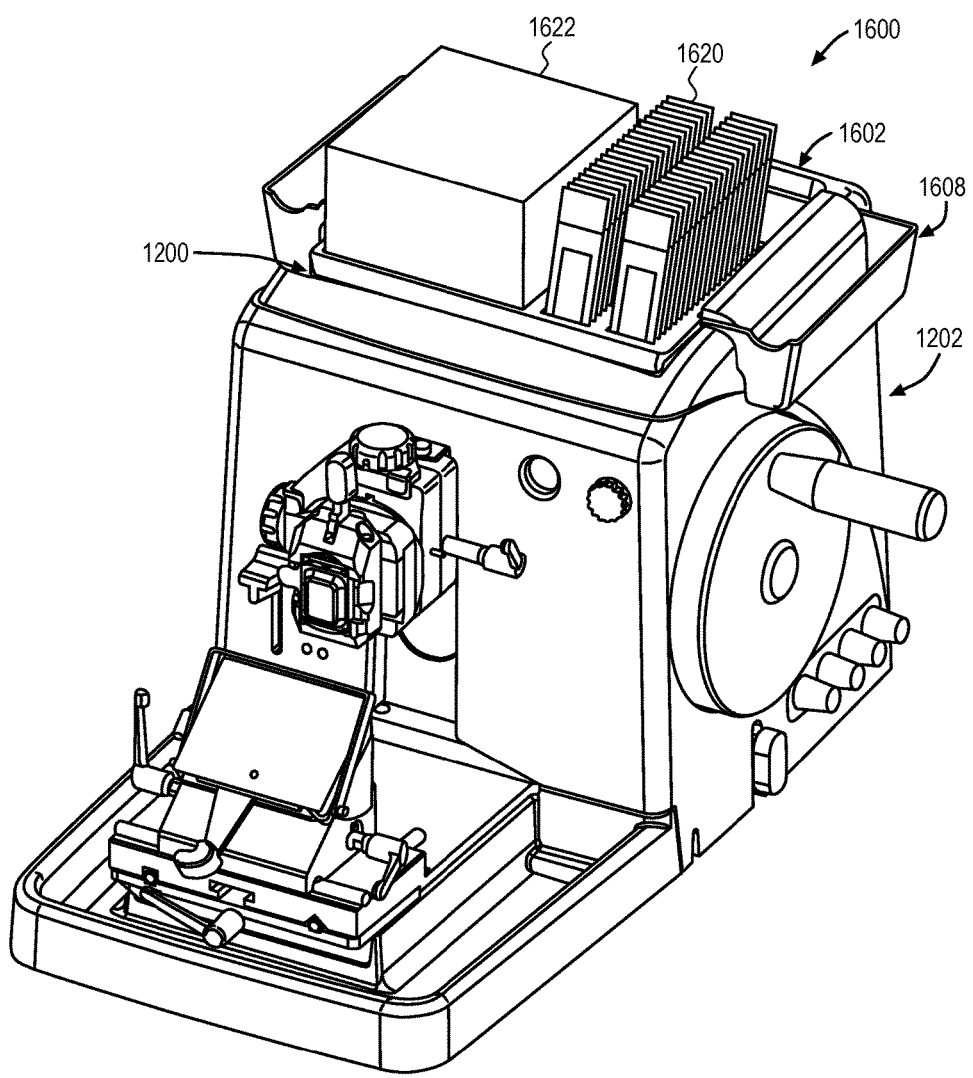
FIG. 16B illustrates a perspective view of another embodiment of a microtome storage member.

FIG. 16A and FIG. 16B illustrate perspective views of another embodiment of a storage member. Representatively, FIG. 16A illustrates a perspective view of another embodiment of a storage member than can be used in addition to, or instead of, storage member 1200, and FIG. 16B illustrates the storage member of FIG. 16A positioned on top of a microtome. Representatively, storage member 1600 in this embodiment, is a tray like structure that is dimensioned to rest on top of microtome 1202, for example, within the recessed regions or cavities formed by storage member 1200. Storage member 1600 may have a receiving member 1602, which is designed to store microtome accessories, and a support member 1608, which is designed to help hold the storage member 1600 on microtome 1202, and may also be used for storage.

Receiving member 1602 may include a storage surface 1604 and a mating surface 1606. Storage surface 1604 may be a top side of receiving member 1602 (e.g., a side that faces away from the microtome) and include various recessed regions or cavities 1610A, 1610B, 1610C dimensioned to retain microtome accessories (e.g., tissue box, slide carrier, slides, elongated instruments or the like). Mating surface 1606 is formed by an opposite side of receiving member 1602 and is dimensioned to mate with recesses formed on a top portion of microtome 1202. For example, mating surface 1606 may include protruding portions that are complimentary to recesses or cavities along the top portion of microtome 1202 (e.g., within storage member 1200) and fit within the cavities to hold storage member 1600 in place.

In some embodiments, cavities 1610C may have slots to retain slides 1620 (see FIG. 16B), therein (e.g., slots 1502 as previously discussed) and further include openings 1612 to allow for liquids to drip through storage member 1600. For example, the cavities 1610C may form a drying rack for microtome accessories such as slides 1620 (see FIG. 16B), which may have a liquid component (e.g., water) that drains off the slide when it is positioned in the rack. Openings 1612 allow for the liquid to drain through member 1600 and not collect within the bottom of the cavities 1610C where it could, for example, be a source for bacterial growth and contaminate the slides. In addition, as shown in FIG. 16B, cavity 1610A may be dimensioned to receive an accessory such as a container 1622 (e.g., tissue box, slide container, or the like).

In some embodiments, a liquid absorbing member 1614 may further be positioned between storage member 1600 the surface of microtome 1202, for example, within recessed region of storage member 1200. In this aspect, when storage member 1600 is placed within member 1200 as shown in FIG. 16B, any liquid that flows through openings 1612 is collected and absorbed by liquid absorbing member 1614. Liquid absorbing member 1614 may be any type of liquid absorbing member, for example, a tissue, a napkin, a paper towel, a piece of cloth, or the like.

In addition, storage member 1600 may further include support member 1608 which extends from receiving member 1602 and overlaps a side of microtome 1202 as shown in FIG. 16B to help hold storage member 1600 in place. Support member 1608 may include a cavity or channel 1616 that can also be used to store microtome accessories along a side of microtome 1202 as shown, as well as other similar features as previously discussed in reference to storage member 1400 of FIG. 14.

As can also be seen from FIG. 16A and FIG. 16B, microtome 1202 may include knobs 1618 to control the operation of light source 116 as previously discussed in reference to, for example, FIG. 1 to FIG. 5.

Figure 17A:
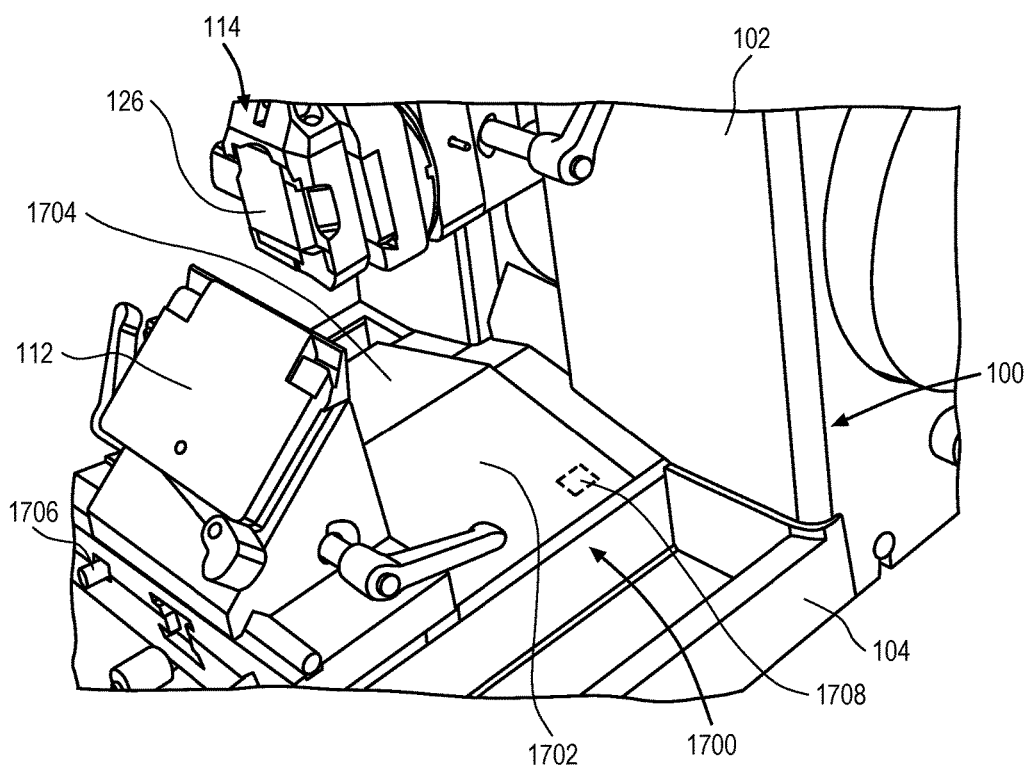
FIG. 17A illustrates a perspective view of one embodiment of a waste removal assembly.
Figure 17B:
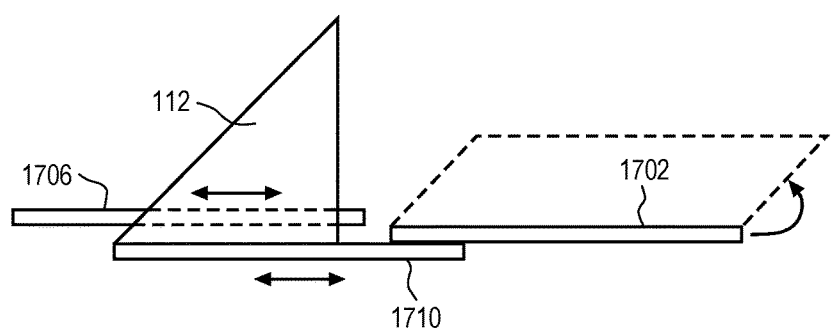
FIG. 17B illustrates a cross-sectional side view of the waste removal assembly of FIG. 17A.
Figure 18:
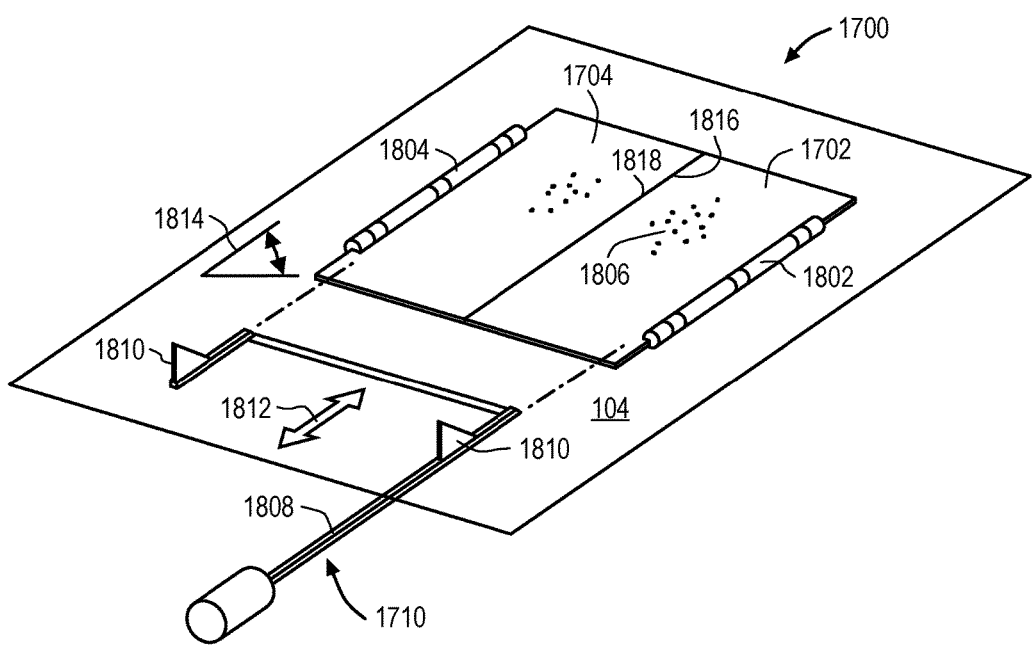
FIG. 18-FIG. 20 illustrate perspective views of an embodiment of a waste removal assembly.

FIG. 17A-FIG. 18 illustrate perspective views of a waste removal assembly for a sample sectioning device. Referring to FIG. 17A-17B, waste removal assembly 1700 may be configured to facilitate removal of waste, such as paraffin debris, that falls onto the surface of microtome 100 during a cutting operation. Microtome 100 may, for example, be substantially similar to microtome 100 described in reference to the previous Figures. Thus, while specific details of microtome 100 are not described and/or shown in FIG. 17A-FIG. 18, it should be understood that they may be included.

Removal assembly 1700 may be positioned on base member 104 of microtome 100, below cutting mechanism 112 and sample holder 114. In this aspect, when sample 126 is sliced by cutting mechanism 112, the sliced sample section remains on the front side of cutting mechanism 112 (e.g., side facing away from base member 104) and any waste falls behind cutting mechanism 112 onto waste removal assembly 1700. Typically, any waste or debris that falls into this area of microtome 100 is difficult to remove because it is between cutting mechanism 112, the front side of microtome, and sample holder 114, and is therefore difficult for the user to reach.

Waste removal assembly 1700, however, solves this problem by providing a mechanism that helps to push the debris out of this area to a location where it is easier for the user to remove. For example, waste removal assembly 1700 may include a first waste member 1702 and a second waste member 1704, in some embodiments, first waste member 1702 and second waste member 1704 are plates that are at angles, or otherwise inclined, with respect to one another, and the base member 104, such that they form a pitched surface below sample holder 114. In this aspect, when the waste falls on first and second waste members 1702, 1704, it slides down the surface of the members, or can be easily brushed down the surface by the user, and away from the cutting mechanism 112 so that it can be easily removed by a user. In one embodiment, first waste member 1702 and second waste member 1704 are fixed with respect to one another in the pitched configuration as shown. In other embodiments, first and second waste member 1702 and 1704 are movable with respect to one another and have a modifiable slope that can be increased or decreased to facilitate removal of debris. For example, in some embodiments, first and second waste members 1702 and 1704 are coupled to an actuator that causes members 1702, 1704 to move with respect to each other.

For example, FIG. 17B illustrates a cross-sectional side view of the waste removal assembly 1700 of FIG. 17A. From this view, it can be seen that an actuator 1710 is connected to second waste member 1704 (and also connected to first waste member 1702 although not seen from this view). The actuator 1710 may further be connected to cutting mechanism 112. In this aspect, when cutting mechanism 112 slides along rails 1706, this in turn causes actuator 1710 to slide, and move members 1702, 1704 with respect to each other, for example from a first (closer to horizontal) position to a second (closer to vertical) position, as illustrated by the dashed lines. The movement of cutting mechanism 112, actuator 1710 and/or operation of members 1702, 1704 may be automated or manual. For example, where a movement of cutting mechanism 112 is automated (e.g., such as in an automated microtome), the movement of actuator 1710 and members 1702, 1704 may further be considered automated. In other embodiments, the movement of cutting mechanism 112, actuator 1710 and/or members 1702, 1704 may be done manually such as by a user holding one or more of these components and moving (e.g., sliding or rotating) them as desired. The operation of actuator 1710 and members 1702, 1704 will be described in more detail in reference to FIG. 18-FIG. 20.

First waste member 1702 and second waste member 1704 may, in some embodiments, be metal plates. In some embodiments, a temperature of the metal plates can be controlled to facilitate removal of the waste thereon. For example, a thermoelectric cooler (TEC) 1708 may optionally be coupled to one or both of members 1702, 1704 to maintain a desired temperate of members 1702, 1704. For example, it may be desirable to cool members 1702, 1704 below a melting temperature of paraffin, such that the waste (which includes paraffin) resting on members 1702 does not melt and stick to the members 1702, 1704. In addition, in some embodiments to further facilitate waste removal, members 1702, 1704 may have a surface coating (e.g., a non-stick coating such as a fluorocarbon polymer) that makes the surface smoother, or otherwise easier, for the waste to slide off of it.

Figure 19:
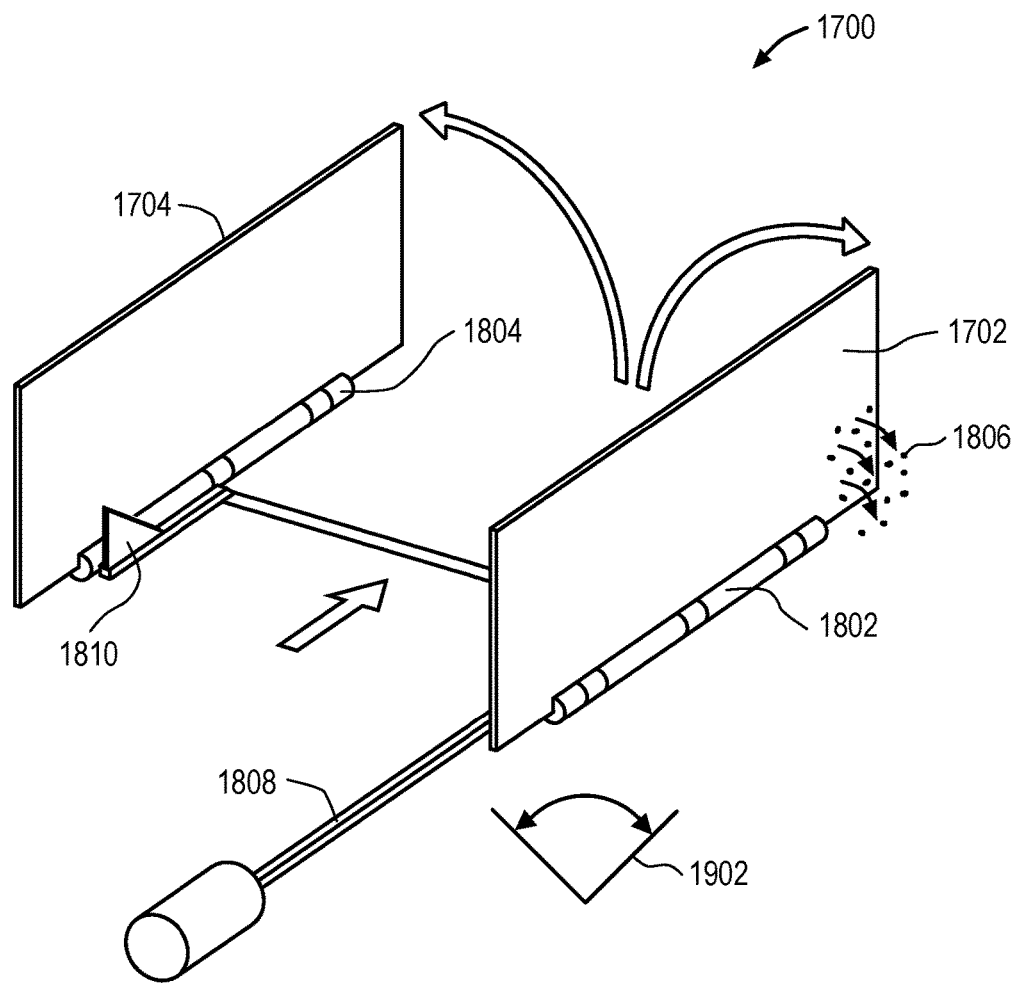
Figure 20:
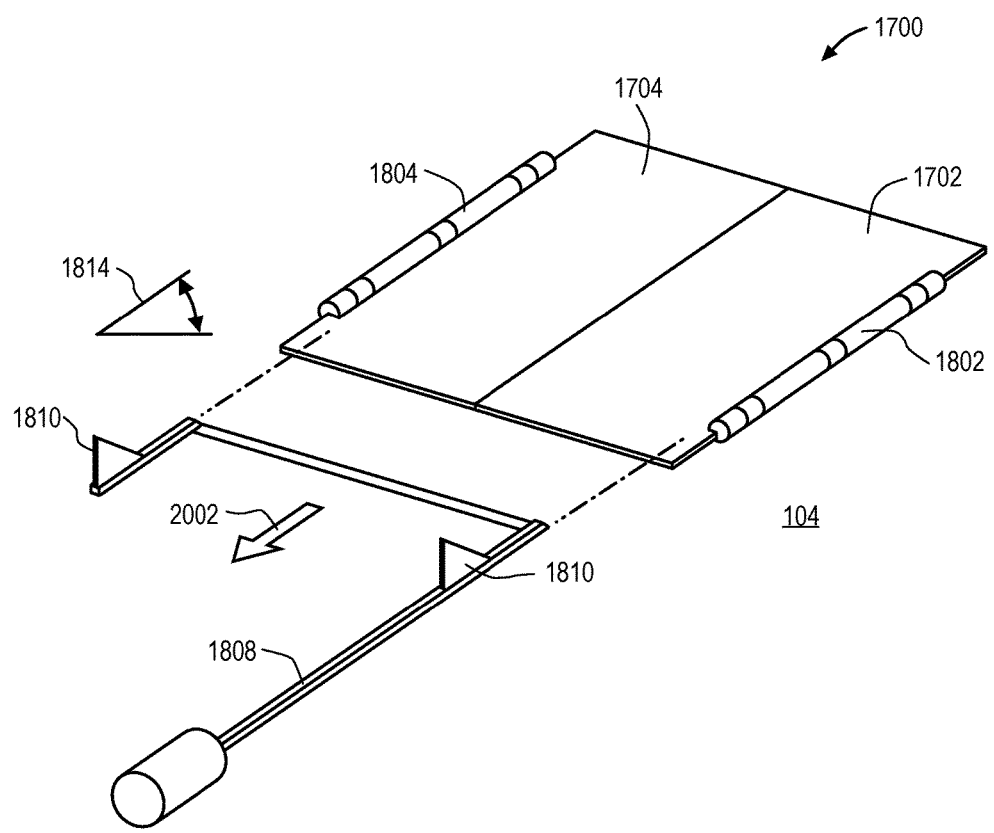

Referring now to FIG. 18-FIG. 20, FIG. 18-FIG. 20 illustrate one embodiment of an operation of a waste removal assembly having movable first and second waste members. Representatively, FIG. 18 shows waste removal assembly 1700 in a first position, for example a waste collecting position, in which an incline of first and second waste members 1702, 1704 is minimal, or there is no incline and members 1702, 1704 are both within a same plane. Any waste or debris 1806 from a cutting operation falls onto first and second waste members 1702, 1704 as shown. First and second waste members 1702, 1704 are attached to the base member 104 (of microtome 100, as previously discussed) at opposite edges by hinges 1802, 1804, respectively. The interfacing edges 1816, 1818 of first and second waste members 1702, 1704, respectively, however, are free and able to move with respect to one another. An actuating member 1710 (e.g., a beam or other elongated structure) including spaced apart protrusions 1810 is positioned in front of each of first and second waste members 1702, 1704. The actuating member 1710 slides toward or away (e.g., horizontally) from first and second waste members 1702, 1704 as shown by arrow 1812 to change the slope or angle of incline of first and second waste members 1702, 1704 with respect to base member 104. In particular, when actuating member 1710 is pushed toward first and second waste members 1702, 1704, protrusions 1810 slide under first and second waste members 1702, 1704 causing them to rotate away from one another (e.g., rotate outwardly or vertically) which, in turn, increases the slope or angle of incline with respect to base member 104 (or horizontal) as shown in FIG. 19. Representatively, FIG. 19 shows first and second waste members 1702, 1704 rotated to a second waste removal position which may be an angle of approximately 90 degrees as shown by angle 1902. Said another way, first and second members 1702, 1704 may rotate within an angle of rotation of approximately 90 degrees (e.g., between 0 degrees to 90 degrees). This, in turn, causes waste members 1702, 1704 (and the surfaces of waste members 1702, 1704) to have a substantially vertical orientation, and therefore debris 1806 to fall off first and second waste members 1702, 1704, and away from the cutting mechanism to an area of microtome 100 where it can be more easily removed. It is noted, however, that although an angle of rotation of approximately 0-90 degrees is disclosed, a greater angle of rotation in which members 1702, 1704 are beyond vertical, for example, from 0-180 degrees, is also contemplated.

Once the debris is removed, actuator 1710 slides away from first and second waste removal members 1702, 1704 as shown by arrow 2002 in FIG. 20 such that they rotate back to the first waste collection position in which the angle of incline 1814 is much smaller than when they are in the removal position (for example, an angle 1814 less than 90 degrees.

Figure 21:
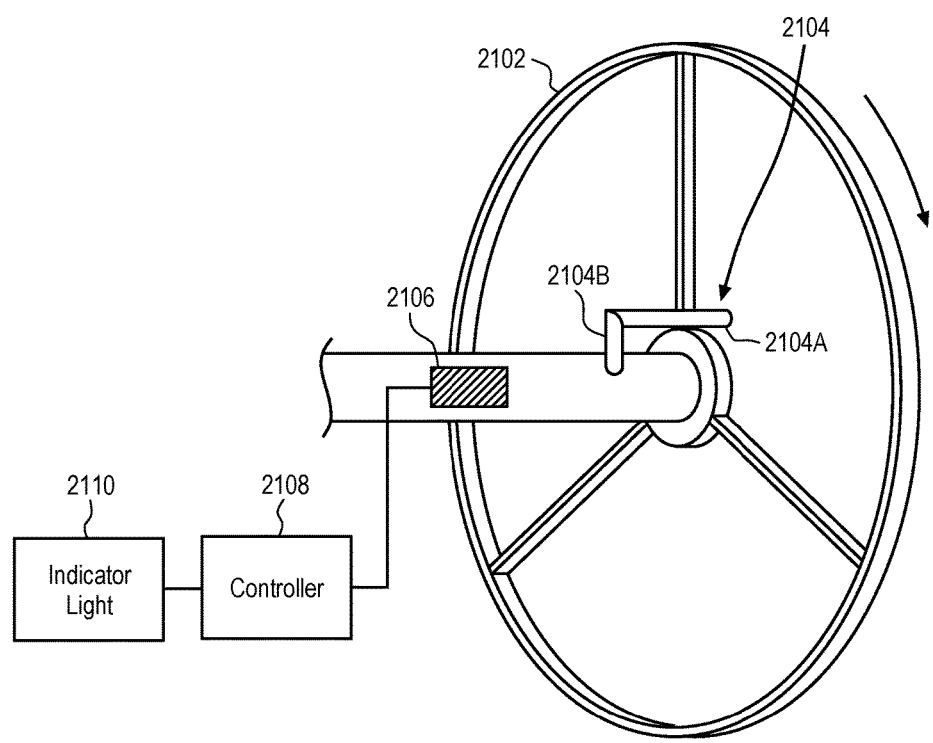
FIG. 21 illustrates a perspective view of an embodiment of a hand wheel lock associated with the sample sectioning device of FIG. 1.

In addition, in some embodiments, the microtome disclosed herein may further include a hand wheel locking mechanism as illustrated by FIG. 21. In particular, after moving the sample holder (e.g., sample holder 114) using a hand wheel 2102 associated with the sample sectioning device (e.g., microtome 100), a locking mechanism 2104 may be engaged to lock the sample holder (e.g., sample holder 114) in the desired position. In some embodiments, the locking mechanism 2104 may also be associated with an indicator light or alarm associated with the microtome, which can be turned on to indicate that the hand wheel is in a locked position. For example, the locking mechanism 2104 may include a tab 2104B that is part of a locking latch 2104A as shown in FIG. 21. In the locked position, when the latch 2104A locks the wheel 2102 in place (e.g., by latching to a wheel spoke or other wheel component), the tab 2104B activates a photo switch 2106 to send a signal to a controller 2108, which in turn, sends a signal to turn on (or off) an indicator light 2110 located on the front of the microtome.

Figure 22:
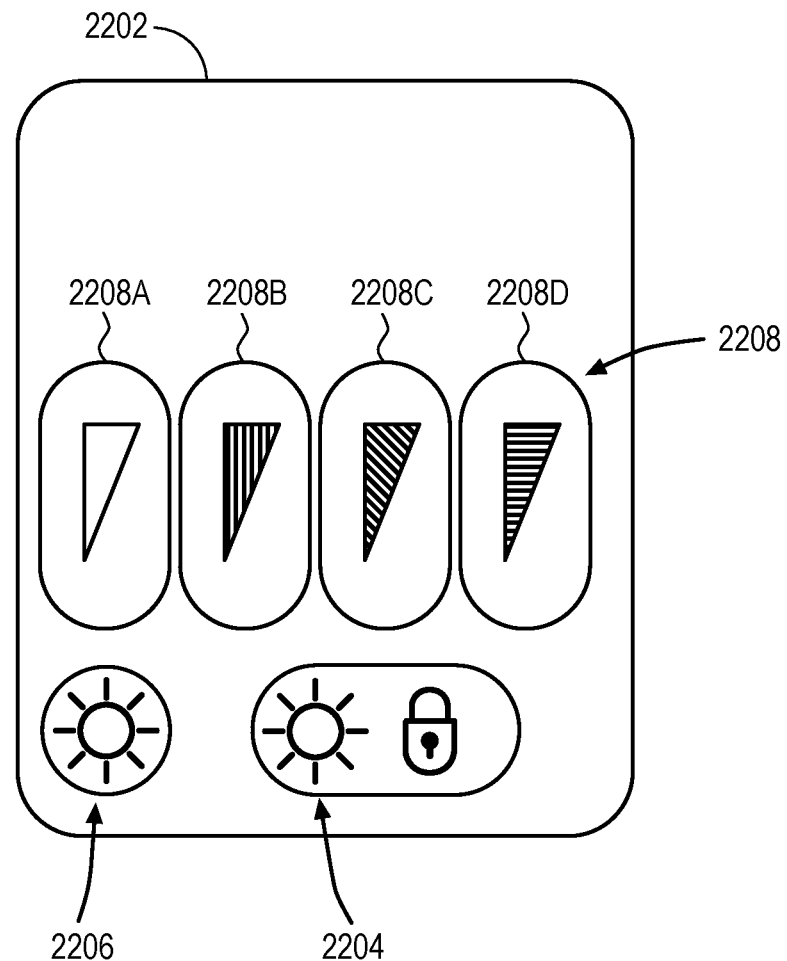
FIG. 22 illustrates a perspective view of an embodiment of a control panel associated with the sample sectioning device of FIG. 1.

FIG. 22 shows one embodiment of an indicator light that may be associated with the locking mechanism of the sample sectioning device. For example, sample sectioning device may include a control panel 2202 associated with the housing (e.g., mounted to housing 102), which includes an indicator light 2204 (e.g., an LED) to indicate the hand wheel is locked, an indicator light 2206 (e.g., an LED) to indicate the light source 116 (behind the specimen block) is on. In addition, the control panel 2202 may also include indicators 2208 to indicate the color, intensity, wavelength, etc. of the light source 116 as previously discussed. For example, indicator 2208A may indicate a light color, indicator 2208B may indicate a light intensity, indicator 2208C may indicate a light wavelength, and indicator 2208D may indicate the amount of time a light has been operating, or a status of a light (e.g., a light is burnt out and needs to be replaced). In other embodiments, each of indicators 2208A-2208D may correspond to, for example, each LED within the light source 116 and indicate a characteristic (e.g., color, intensity, brightness, wavelength or the like) of that specific LED. For example, indicator 2208A may indicate a characteristic of a red LED, indicator 2208B may indicate a characteristic of a blue LED, indicator 2208C may indicate a characteristic of a green LED, and indicator 2208D may indicate a characteristic of a white LED. In other embodiments, indicators 2208A-2208D may be touch sensitive controllers, buttons, or switches, that can receive user input to control different characteristics of the light source 116. In addition, it is contemplated that although the indicator light 2206 is described as a light source different than light source 116, in some embodiment, the indicator light 2206 may be the light source 116 previously discussed in reference to FIG. 1.

In addition, although a mechanical locking mechanism is discussed in reference to FIG. 21, in some embodiments, the locking mechanism may be, for example, a permanent magnet solenoid, a geared motor or a rotating handle that locks by friction or other known manner. In one embodiment, a motor may be used to tighten the chuck at times when the chuck is not being adjusted. When the microtome determines to adjust the position of the sample by adjusting the chuck, or when a user decides to manually adjust the position of the tissue sample by adjusting the chuck, a motor may be signaled to loosen the chuck to allow the chuck to be adjusted. At other times, when the position of the chuck is not being adjusted, a motor may be signaled to maintain the chuck in a tightened or locked configuration so that the position of the chuck and/or the position of a sample held by the chuck do not change unintentionally.

It should be understood that in some embodiments, sample holder may be any sample holder capable of realigning an orientation of a surface of a sample so that it is parallel or more parallel with a cutting member and/or a cutting plane. For example, in some embodiments, the sample holder may be part of a multi-axis workpiece chuck or motorized chuck that is capable of adjusting an orientation of the cutting surface of the sample in two dimensions relative to a cutting member and/or cutting plane. Examples of suitable multi-axis workpiece chucks are described in U.S. Pat. No. 7,168,694, entitled "MULTI-AXIS WORKPIECE CHUCK," by Xuan S. Bui et al., filed on Jan. 22, 2004, and assigned to the assignee of the present application. In one embodiment, the multi-axis chuck may have a mounting assembly that retains a workpiece, such as a sample, in a substantially fixed orientation with respect to the chuck. The chuck may be rotated manually by an operator using a controller that is in communication with one or more motors, or the microtome may autonomously rotate the chuck. One or more sensors may be used to sense a position of the chuck. According to one embodiment, each axis may have three sensors that detect a middle nominal position and end positions of the chuck. A user or the microtome may control movement of the chuck by signaling the motor to rotate the chuck to the desired position. The sensors may be used to determine whether the desired position has been reached. In one embodiment, the chuck may include first and second portions that are rotatable about at least two orthogonal axes. The first portion may rotate about a first axis and independently of the second portion. Rotation of the second portion about a second axis may cause the first portion to rotate about the second axis also. This may allow the chuck to be rotatable in multiple dimensions.

In some embodiments, a sample cutting or sectioning cycle may include: (1) moving a sample block in a forward horizontal direction toward the cutting plane a predetermined distance related to the desired slice thickness; (2) moving the sample block in a vertical direction (for example downward) toward the cutting member to obtain a slice; (3) moving the sample block in a backward or opposite horizontal direction away from the cutting plane and/or cutting member a predetermined distance; and (4) moving sample block in an opposite vertical direction (for example upward) away from the cutting member. Retracting or moving the sample block in a backward horizontal direction away from the cutting member helps to avoid the sample block contacting the cutting member during (4) when moving sample block in the opposite vertical direction (for example upward) away from the cutting member. Representatively, the distance sample block is retracted may correspond to a thickness of the sliced sample. Alternatively, it is contemplated that in some embodiments, the retraction step may be omitted. The slicing cycle may be repeated until a desired number of slices are obtained.

In some embodiments, the microtome may be capable of using different speeds of movement of a sample for different portions of a sectioning cycle. For example, in some embodiments, a relatively faster speed of movement of the feed drive system and/or a sample may be used during one or more non-sectioning portions of a sectioning cycle (e.g., where cutting or sectioning of a sample is not performed), whereas a relatively slower speed of movement of the feed drive system and/or a sample may be used during a sectioning portion of the sectioning cycle (e.g., where cutting or sectioning of the sample is performed). Using a relatively slower speed of movement of the feed drive system and/or sample during cutting or sectioning of the sample tends to provide higher quality sections and/or more consistent sections, whereas performing one or more other non-sectioning portions of the sectioning cycle more rapidly may help to improve the overall speed of the sectioning cycle and/or may allow more sections to be produced in a given amount of time. As such, the speed of movement of a feed drive system and/or a sample may vary throughout a sectioning cycle. For example, a user may control or program a sectioning cycle so that movement of sample block or sample in a vertical direction (for example downward) toward the cutting member to obtain a slice (e.g., operation (2) in the paragraph above) is performed more slowly than one or more other portions of the sectioning cycle (e.g., operations (1), (3), (4), or a combination thereof, in the paragraph above).

In some embodiments, the microtome may include logic to control an operation of the light source associated with the sample holder. For example, in some embodiments, the microtome may include logic to allow a configurable or programmable brightness or color selection to be configured or programmed. By way of example, the brightness or color may be selected based upon a color or other characteristic of the sample. In one example embodiment, the microtome may be operable to allow an operator to specify or indicate the type of sample, characteristic of the sample (e.g., color) or characteristic of the embedding medium. The microtome may include logic which is programmed to, based on this information, select a brightness and/or color of the light to be output which has been determined to allow for a desired level of contrast between, for example, the tissue or tissue characteristics and the embedding medium (e.g., paraffin). In other embodiments, the brightness or color output from the light source may be manually selected by the user.

In some embodiments, the microtome may include logic to allow a configurable or programmable sectioning portion of a sectioning cycle to be specified over which relatively slower speed of movement of the feed drive system and/or a sample are to be used. For example, in some embodiments, the microtome may include logic to allow a configurable or programmable sectioning length to be configured or programmed. By way of example, the length may be selected from among a plurality of predetermined lengths corresponding to different types of cassettes having different dimensions. Different types of cassettes have different sectioning lengths over which sectioning is performed. As one example, 7019 Paraform® brand Biopsy 13 mm×13 mm Cassettes, and 7020 Paraform® brand Biopsy 26 mm×19 mm Cassettes, which are commercially available from Sakura Finetek USA, Inc., of Torrance, Calif., have different sectioning lengths. In one example embodiment, the microtome may be operable to allow an operator to specify or indicate a sectioning length. The specification or indication of the sectioning length may be done in different ways, such as, for example, by specifying a length, selecting a length from among a plurality of predetermined lengths, specifying a type of cassette, selecting a type of cassette from among a plurality of different types of cassettes, etc. For example, when a user is ready to product sections from a particular type of cassette, the user may make a selection of the particular type of cassette using a control device, and the microtome may already be preprogrammed with a predetermined sectioning length corresponding to that particular type of cassette. During sectioning, the microtome may use a relatively slower speed of movement of the feed drive system and/or the sample over the specified sectioning length and may use relatively faster speeds of movement over one or more or substantially all other portions of the sectioning cycle. For example, immediately or just before and immediately or just after the cutting of the sample over the specified sectioning length the relatively faster speeds may be used.

In some embodiments, a microtome may include logic to initially autonomously remove a given or predetermined portion of a sample. For example, the portion may include a given or predetermined thickness of paraffin, embedding material, cassette material, or other non-tissue material overlying or concealing the actual tissue material from which a section is desired to be taken (e.g., disposed between a cutting surface of the tissue material and the foremost external surface of the sample which would contact a sensing plate). By way of example, a sample may include a piece of tissue placed on a bottom of a cassette and the cassette and the tissue sample embedded in a block of embedding material. In the case of various cassettes manufactured by Sakura Finetek USA, Inc., of Torrance, Calif., the cassettes may include a Paraform® brand cassette material that has sectioning characteristics similar to that of paraffin and sectioning may be performed through the Paraform® brand cassette material of the cassette bottom.

In some embodiments, a microtome may include logic to initially autonomously remove a given or predetermined portion of a sample, for example, a portion of paraffin, embedding material, cassette material, or other non-tissue material overlying or concealing an actual tissue material desired to be sectioned. For example, the microtome may autonomously remove a bottom of a cassette in order to expose or provide access to the actual tissue material of the sample. Representatively, in the case of certain cassettes, depending upon the thickness of the material making up the bottom of the cassette and the thickness of the sections, the microtome may autonomously make a plurality (e.g., from around two to about twenty, often from about five to about fifteen) of sections to remove a predetermined thickness of the bottom of the cassette. The thickness of the bottom of the cassette may be known by the microtome or predetermined. For example, a user may specify the thickness directly, or select a type of cassette from among several different types that each has a preprogrammed or otherwise known cassette bottom thickness. In some cases, the operator may control the microtome to perform the automated process, for example, with a user input device (e.g., a trim button) on a control device or otherwise selecting a trim operation. Advantageously, allowing the microtome to autonomously remove the portion of the sample (e.g., the bottom of the cassette) may relive the operator from having to do so and/or may tend to speed up the removal of the portion of the sample (e.g., the bottom of the cassette). Then, once the actual tissue of the sample is exposed, a sectioning cycle to obtain slices or sections of the tissue may be commenced (e.g., the operator may press a section button or otherwise cause the microtome to take a section from the now exposed cutting surface of the tissue sample.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense.

In the description above, for the purposes of explanation, numerous specific details have been set forth in order to provide a thorough understanding of the embodiments of the invention. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known circuits, structures, devices, and operations have been shown in block diagram form or without detail in order to avoid obscuring the understanding of the description.

It will also be appreciated, by one skilled in the art, that modifications may be made to the embodiments disclosed herein, such as, for example, to the sizes, shapes, configurations, couplings, forms, functions, materials, and manner of operation, and assembly and use, of the components of the embodiments. All equivalent relationships to those illustrated in the drawings and described in the specification are encompassed within embodiments of the invention. Further, where considered appropriate, reference numerals or terminal portions of reference numerals have been repeated among the figures to indicate corresponding or analogous elements, which may optionally have similar characteristics.

Various operations and methods have been described. Some of the methods have been described in a basic form, but operations may optionally be added to and/or removed from the methods. In addition, while a particular order of the operations according to example embodiments has been described, it is to be understood that that particular order is exemplary. Alternate embodiments may optionally perform the operations in different order, combine certain operations, overlap certain operations, etc. Many modifications and adaptations may be made to the methods and are contemplated.

One or more embodiments include an article of manufacture (e.g., a computer program product) that includes a machine-accessible and/or machine-readable medium. The medium may include, a mechanism that provides (e.g., stores) information in a form that is accessible and/or readable by the machine. The machine-accessible and/or machine-readable medium may provide, or have stored thereon, a sequence of instructions and/or data structures that if executed by a machine causes or results in the machine performing, and/or causes the machine to perform, one or more or a portion of the operations or methods disclosed herein. In one embodiment, the machine-readable medium may include a tangible non-transitory machine-readable storage media. For example, the tangible non-transitory machine-readable storage media may include a floppy diskette, an optical storage medium, an optical disk, a CD-ROM, a magnetic disk, a magneto-optical disk, a read only memory (ROM), a programmable ROM (PROM), an erasable-and-programmable ROM (EPROM), an electrically-erasable-and-programmable ROM (EEPROM), a random access memory (RAM), a static-RAM (SRAM), a dynamic-RAM (DRAM), a Flash memory, a phase-change memory, or a combinations thereof. The tangible medium may include one or more solid or tangible physical materials, such as, for example, a semiconductor material, a phase change material, a magnetic material, etc.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A sample sectioning device comprising:
a housing having a base member;
a cutting mechanism positioned on the base member and operable to cut sections from a sample;
a sample holder dimensioned to hold a sample and operable to move with respect to the cutting mechanism during a cutting operation; and
a waste removal assembly positioned below the cutting mechanism and the sample holder, the waste removal assembly having a first member and a second member that are dimensioned to remove waste produced during the cutting operation,
wherein the first member and the second member are each movably connected to the base member and operable to move between a first position in which they are at a first angle with respect to the base member and a second position in which they are at a second angle with respect to the base member, wherein the second angle is greater than the first angle.

2. A sample sectioning device comprising:
a housing having a base member;
a cutting mechanism positioned on the base member and operable to cut sections from a sample;
a sample holder dimensioned to hold a sample and operable to move with respect to the cutting mechanism during a cutting operation; and
a waste removal assembly positioned below the cutting mechanism and the sample holder, the waste removal assembly having a first member and a second member that are dimensioned to remove waste produced during the cutting operation,
wherein the first member and the second member are operable to move with respect to the base member between a first angle of incline and a second angle of incline, wherein the second angle of incline is approximately 90 degrees and is greater than the first angle of incline.

3. A sample sectioning device comprising:
a housing having a base member;
a cutting mechanism positioned on the base member and operable to cut sections from a sample;
a sample holder dimensioned to hold a sample and operable to move with respect to the cutting mechanism during a cutting operation; and
a waste removal assembly positioned below the cutting mechanism and the sample holder, the waste removal assembly having a first member and a second member that are dimensioned to remove waste produced during the cutting operation,
wherein the cutting mechanism is operable to slide with respect to the base member, and wherein sliding of the cutting mechanism causes the first member and the second member to move with respect to one another.

4. A sample sectioning device comprising:
a housing having a base member;
a cutting mechanism positioned on the base member and operable to cut sections from a sample;
a sample holder dimensioned to hold a sample and operable to move with respect to the cutting mechanism during a cutting operation; and
a waste removal assembly positioned below the cutting mechanism and the sample holder, the waste removal assembly having a first member and a second member that are dimensioned to remove waste produced during the cutting operation,
wherein the first member and the second member comprise a position wherein each are at an angle of incline greater than 0 degrees with respect to the base member and comprise an interfacing edge to form a pitched surface below the cutting mechanism and the sample holder.

5. The sample sectioning device of claim 4 wherein the first member and the second member are fixed with respect to one another.

6. The sample sectioning device of claim 4 further comprising: a temperature controlling member coupled to the first member or the second member to control a temperature thereof.

7. A waste removal assembly for a sample sectioning device comprising:
a first inclined member coupled to a microtome housing;
a second inclined member coupled to a microtome housing; and
an actuator movably coupled to the first inclined member and the second inclined member, wherein the actuator is operable to cause a slope of one of the first inclined member or the second inclined member to change.

8. The waste removal assembly of claim 7 wherein the first inclined member and the second inclined member comprise metal plates.

9. The waste removal assembly of claim 7 wherein one of the first inclined member or the second inclined member comprises a plate having an edge that is coupled to the sample sectioning device by a hinge.

10. The waste removal assembly of claim 7 wherein the slope of the first inclined member or the second inclined member is a first slope, and the actuator causes the first inclined member or the second inclined member to change to a second slope, wherein the second slope is greater than the first slope.

11. The waste removal assembly of claim 7 wherein the actuator causes the slope of one of the first inclined member or the second inclined member to change within a range of ninety degrees with respect to horizontal.

12. The waste removal assembly of claim 7 wherein the actuator comprises a cutting mechanism of the sample sectioning device, and wherein a sliding of the cutting mechanism causes the slope of one of the first inclined member or the second inclined member to change.

13. The waste removal assembly of claim 7 wherein the actuator comprises an actuating member and a protrusion, wherein the actuating member slides the protrusion under the first inclined member and the second inclined member to change the slope.

14. The waste removal assembly of claim 7 wherein the actuator is manually operated by a user.

15. The waste removal assembly of claim 7 the actuator is automated.

16. The waste removal assembly of claim 7 further comprising:
a thermoelectric cooler (TEC) coupled to the first member or the second member to control a temperature thereof.

* * * * *